United States Patent
Danling et al.

(10) Patent No.: US 10,994,008 B2
(45) Date of Patent: May 4, 2021

(54) MODULATION OF TUMOR IMMUNITY

(71) Applicant: Merck Sharp & Dohme Corp., Rahway, NJ (US)

(72) Inventors: Gu Danling, San Jose, CA (US); Amy M. Beebe, Half Moon Bay, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 163 days.

(21) Appl. No.: 15/926,035

(22) Filed: Mar. 20, 2018

(65) Prior Publication Data

US 2018/0207266 A1 Jul. 26, 2018

Related U.S. Application Data

(62) Division of application No. 14/912,733, filed as application No. PCT/US2014/051402 on Aug. 18, 2014, now Pat. No. 10,188,729.

(60) Provisional application No. 61/867,976, filed on Aug. 20, 2013.

(51) Int. Cl.
| A61K 39/39 | (2006.01) |
| A61K 39/395 | (2006.01) |
| C07K 16/28 | (2006.01) |
| A61K 39/00 | (2006.01) |

(52) U.S. Cl.
CPC ...... *A61K 39/3955* (2013.01); *C07K 16/2818* (2013.01); *C07K 16/2878* (2013.01); *A61K 2039/505* (2013.01); *A61K 2039/507* (2013.01); *A61K 2039/545* (2013.01); *C07K 2317/75* (2013.01); *C07K 2317/76* (2013.01)

(58) Field of Classification Search
CPC ........ A61K 2039/505; A61K 2039/507; C07K 2317/75
See application file for complete search history.

(56) References Cited

U.S. PATENT DOCUMENTS

| 5,141,736 | A | 8/1992 | Iwasa et al. |
| 8,114,845 | B2 | 2/2012 | Langermann et al. |
| 8,709,424 | B2 | 4/2014 | Schebye et al. |
| 2007/0098719 | A1 | 5/2007 | Smith et al. |
| 2012/0189639 | A1* | 7/2012 | Schebye .......... A61P 31/14 424/158.1 |
| 2013/0071403 | A1* | 3/2013 | Rolland .......... A61K 45/06 424/142.1 |
| 2014/0348841 | A1 | 11/2014 | Schebye et al. |

FOREIGN PATENT DOCUMENTS

| CN | 102203132 A | 9/2011 |
| CN | 102227447 A | 10/2011 |
| JP | 2008278814 | 11/2008 |
| WO | WO2006105021 | 10/2006 |
| WO | WO2010040105 A2 | 4/2010 |
| WO | WO2010027423 A3 | 5/2010 |
| WO | WO201128683 | 3/2011 |
| WO | WO2011028683 * | 3/2011 |
| WO | WO2011028983 A1 | 3/2011 |
| WO | WO2011130753 | 10/2011 |
| WO | WO2011159877 | 12/2011 |
| WO | 2013019906 | 2/2013 |
| WO | WO2013043569 | 3/2013 |
| WO | WO2013063516 A1 | 5/2013 |
| WO | 2015026684 A1 | 2/2015 |
| WO | W02015112900 | 7/2015 |
| WO | WO2015112800 A1 | 7/2015 |
| WO | WO2015031667 A3 | 11/2015 |

OTHER PUBLICATIONS

Paul, Fundamental Immunology, 3rd Edition, 1993, pp. 292-295, under the heading Fv Structure and Diversity in Three Dimensions (Year: 1993).*
Rudikoff et al, Proc. Natl. Acad. Sci. USA 1982 vol. 79: p. 1979 (Year: 1979).*
Casset et al, BBRC 307, 198-205 2003 (Year: 2003).*
Pascalis et al (The Journal of Immunology vol. 169, 3076-3084, 2002 (Year: 2002).*
Melero et al, Clin Cancer Res 19:997-1008, Mar. 1, 2013. (Year: 2013).*
Vanneman et al., Combining immunotherapy and targeted therapies in cancer treatment, Nature Reviews/Cancer, 2012, pp. 237-251, vol. 12.
Brennan et al., Preparation of Bispecific Antibodies by Chemical Recombination of Monoclonal Immunoglobulin Fragments, Science, 1985, pp. 81-83, vol. 229.
Casset, A peptide mimetic of an anti-CD4 monoclonal antibody by rational design, BBRC, 2003, pp. 198-205, vol. 307.
Holliger et al., Diabodies, Proc. Natl. Acad. Sci. USA, 1993, No. 14, pp. 6444-6448, vol. 90.
Ko et al, Treatment of advanced tumors with agonistic anti-GITR mAb and its effects on tumor-infiltrating Foxp3 +CD25+CD4+ regulatory T cells, J. Exp. Med., 2005, 885-891, vol. 202(7).
Lei et al., Combined PD-1 blockade and GITR triggering induce a potent antitumor immunity in murine cancer models and synergizes with chemotherapeutic drugs, J. Translational Med., 2014, 36, vol. 12(1).
Melero et al., Agonist Antibodies to TNFR Molecules That Costimulate T and NK Cells, Clin. Cancer Res., 2013, pp. 1044-1053, vol. 19.
Melero I, Grimaldi AM, Perez-Gracia JL, Ascierto PA., Clinical development of immunostimulatory monoclonal antibodies and opportunities for combination, Clin Cancer Res, 2013, 997-1008, vol. 19(5).
Partial Translation of Claims—W02015/112800 filed Jul. 30, 2015—Regeneron Pharmaceuticals Inc., 2008, pp. 1-4.

(Continued)

*Primary Examiner* — Lei Yao
(74) *Attorney, Agent, or Firm* — Yingying Zeng; John C. Todaro

(57) ABSTRACT

Methods of treating proliferative disorders are described. In particular, combination treatment with a GITR agonist and a PD-1 antagonist are provided.

7 Claims, 15 Drawing Sheets

Specification includes a Sequence Listing.

(56) References Cited

OTHER PUBLICATIONS

Pascalis et al., Grafting of "Abbreviated" Complementarity-DeterminingRegions Containing Specificity-Determining Residues Essential for Ligand Contact to Engineer a Less Immunogenic Humanized Monoclonal Antibody, The Journal of Immunology, 2002, pp. 3076-3084, vol. 169.
Paul, WE, Fundamental Immunology, Fundamental Immunolgy, third edition, 1993, 292-295, Third Edition.
Rudikoff, Single amino acid substitution altering antigen-binding specificity, Proc. Natl. Acad. Sci. USA, 1982, pp. 1979-1983, vol. 79.
Schaer DA, Murphy JT, Wolchok JD., Modulation of GITR for cancer immunotherapy, Curr Opin Immunol., 2012, 217-224, vol. 24(2).
Hamid, et al., Safety and Tumor Responses with Lambrolizumab Anti-PD-1 in Melanoma., N. Engl. J. Med., 2013, vol. 369, pp. 134-144.
U.S. Appl. No. 14/912,733, filed Feb. 18, 2016.

* cited by examiner

SEQUENCE LISTING

```
<160> NUMBER OF SEQ ID NOS: 88

<210> SEQ ID NO 1
<211> LENGTH: 10
<212> TYPE: PRT
<213> ORGANISM: Mus musculus

<400> SEQUENCE: 1

Gly Phe Thr Phe Ser Ser Tyr Ala Met Ser
1               5                   10

<210> SEQ ID NO 2
<211> LENGTH: 10
<212> TYPE: PRT
<213> ORGANISM: Rattus norvegicus

<400> SEQUENCE: 2

Gly Phe Thr Phe Ser Asp Tyr Tyr Met Ala
1               5                   10

<210> SEQ ID NO 3
<211> LENGTH: 11
<212> TYPE: PRT
<213> ORGANISM: Mus musculus

<400> SEQUENCE: 3

Gly Tyr Ser Ile Thr Ser Asp Tyr Ala Trp Asn
1               5                   10

<210> SEQ ID NO 4
<211> LENGTH: 10
<212> TYPE: PRT
<213> ORGANISM: Mus musculus

<400> SEQUENCE: 4

Gly Tyr Thr Phe Ser Arg Tyr Trp Ile Glu
1               5                   10

<210> SEQ ID NO 5
<211> LENGTH: 10
<212> TYPE: PRT
<213> ORGANISM: Mus musculus

<400> SEQUENCE: 5

Gly Tyr Thr Phe Thr Ser Tyr Thr Met His
1               5                   10

<210> SEQ ID NO 6
```

```
<211> LENGTH: 12
<212> TYPE: PRT
<213> ORGANISM: Mus musculus

<400> SEQUENCE: 6

Gly Phe Ser Leu Ser Thr Ser Gly Met Gly Val Gly
1               5                   10

<210> SEQ ID NO 7
<211> LENGTH: 10
<212> TYPE: PRT
<213> ORGANISM: Mus musculus

<400> SEQUENCE: 7

Gly Phe Thr Val Arg Asn Tyr Ala Met Ser
1               5                   10

<210> SEQ ID NO 8
<211> LENGTH: 10
<212> TYPE: PRT
<213> ORGANISM: Mus musculus

<400> SEQUENCE: 8

Gly Asp Ser Ile Thr Ser Gly Tyr Trp Asn
1               5                   10

<210> SEQ ID NO 9
<211> LENGTH: 10
<212> TYPE: PRT
<213> ORGANISM: Mus musculus

<400> SEQUENCE: 9

Gly Asp Ser Ile Thr Ser Gly Tyr Trp Asn
1               5                   10

<210> SEQ ID NO 10
<211> LENGTH: 12
<212> TYPE: PRT
<213> ORGANISM: Rattus norvegicus

<400> SEQUENCE: 10

Gly Phe Ser Leu Ser Thr Tyr Gly Val Gly Val Gly
1               5                   10

<210> SEQ ID NO 11
<211> LENGTH: 12
<212> TYPE: PRT
<213> ORGANISM: Rattus norvegicus

<400> SEQUENCE: 11

Gly Phe Ser Leu Ser Thr Tyr Gly Val Gly Val Gly
1               5                   10

<210> SEQ ID NO 12
<211> LENGTH: 16
<212> TYPE: PRT
<213> ORGANISM: Mus musculus

<400> SEQUENCE: 12

Ser Ile Ser Ser Gly Gly Thr Thr Tyr Tyr Pro Asp Ser Val Lys Gly
1               5                   10                  15

<210> SEQ ID NO 13
<211> LENGTH: 17
<212> TYPE: PRT
```

<213> ORGANISM: Rattus norvegicus

<400> SEQUENCE: 13

Tyr Ile His Ala Asn Gly Gly Ser Thr Tyr Tyr Arg Asp Ser Val Arg
1               5                   10                  15
Gly

<210> SEQ ID NO 14
<211> LENGTH: 16
<212> TYPE: PRT
<213> ORGANISM: Mus musculus

<400> SEQUENCE: 14

Tyr Ile Ser Tyr Ser Gly Ser Thr Arg Tyr Asn Pro Ser Leu Lys Ser
1               5                   10                  15

<210> SEQ ID NO 15
<211> LENGTH: 17
<212> TYPE: PRT
<213> ORGANISM: Mus musculus

<400> SEQUENCE: 15

Glu Ile Leu Pro Gly Ser Gly Ser Ser Asn Tyr Asn Glu Lys Phe Lys
1               5                   10                  15
Asp

<210> SEQ ID NO 16
<211> LENGTH: 17
<212> TYPE: PRT
<213> ORGANISM: Mus musculus

<400> SEQUENCE: 16

Tyr Ile Asn Pro Arg Ser Val Tyr Thr Asn Tyr Asn Gln Lys Phe Lys
1               5                   10                  15
Asp

<210> SEQ ID NO 17
<211> LENGTH: 16
<212> TYPE: PRT
<213> ORGANISM: Mus musculus

<400> SEQUENCE: 17

His Ile Trp Trp Asp Asp Asp Lys Tyr Tyr Ser Pro Ser Leu Lys Ser
1               5                   10                  15

<210> SEQ ID NO 18
<211> LENGTH: 16
<212> TYPE: PRT
<213> ORGANISM: Mus musculus

<400> SEQUENCE: 18

Ser Ile Ser Thr Gly Asp Arg Ser Tyr Leu Pro Asp Ser Met Lys Gly
1               5                   10                  15

<210> SEQ ID NO 19
<211> LENGTH: 16
<212> TYPE: PRT
<213> ORGANISM: Mus musculus

<400> SEQUENCE: 19

Tyr Ile Ser Tyr Ser Gly Ser Thr Tyr Tyr Asn Pro Ser Leu Arg Gly
1               5                   10                  15

<210> SEQ ID NO 20
<211> LENGTH: 16
<212> TYPE: PRT
<213> ORGANISM: Mus musculus

<400> SEQUENCE: 20

Phe Ile Ser Tyr Ser Gly Asn Thr Tyr Tyr Asn Pro Ser Leu Arg Ser
1               5                   10                  15

<210> SEQ ID NO 21
<211> LENGTH: 16
<212> TYPE: PRT
<213> ORGANISM: Rattus norvegicus

<400> SEQUENCE: 21

Asn Ile Trp Trp Asp Asp Asp Asn Tyr Tyr Asn Pro Ser Leu Ile His
1               5                   10                  15

<210> SEQ ID NO 22
<211> LENGTH: 16
<212> TYPE: PRT
<213> ORGANISM: Rattus norvegicus

<400> SEQUENCE: 22

Asn Ile Trp Trp Asp Asp Asp Lys Tyr Tyr Asn Pro Ser Leu Lys Asn
1               5                   10                  15

<210> SEQ ID NO 23
<211> LENGTH: 10
<212> TYPE: PRT
<213> ORGANISM: Mus musculus

<400> SEQUENCE: 23

Val Gly Gly Tyr Tyr Asp Ser Met Asp Tyr
1               5                   10

<210> SEQ ID NO 24
<211> LENGTH: 14
<212> TYPE: PRT
<213> ORGANISM: Rattus norvegicus

<400> SEQUENCE: 24

Gly Ser Phe Met Tyr Ala Ala Asp Tyr Tyr Ile Met Asp Ala
1               5                   10

<210> SEQ ID NO 25
<211> LENGTH: 9
<212> TYPE: PRT
<213> ORGANISM: Mus musculus

<400> SEQUENCE: 25

Gln Leu Gly Leu Arg Phe Phe Asp Tyr
1               5

<210> SEQ ID NO 26
<211> LENGTH: 9
<212> TYPE: PRT
<213> ORGANISM: Mus musculus

<400> SEQUENCE: 26

Lys Val Tyr Tyr Tyr Ala Met Asp Phe
1               5

<210> SEQ ID NO 27

```
<211> LENGTH: 10
<212> TYPE: PRT
<213> ORGANISM: Mus musculus

<400> SEQUENCE: 27

Leu Gly Gly Tyr Tyr Asp Thr Met Asp Tyr
1               5                   10

<210> SEQ ID NO 28
<211> LENGTH: 23
<212> TYPE: PRT
<213> ORGANISM: Mus musculus

<400> SEQUENCE: 28

Ser Tyr Tyr Tyr Gly Ser Ser Gly Ala Met Asp Tyr Trp Gly Gln Gly
1               5                   10                  15

Thr Ser Val Thr Val Ser Ser
            20

<210> SEQ ID NO 29
<211> LENGTH: 20
<212> TYPE: PRT
<213> ORGANISM: Mus musculus

<400> SEQUENCE: 29

Tyr Phe Asp Phe Asp Ser Phe Ala Phe Trp Gly Gln Gly Thr Leu Val
1               5                   10                  15

Thr Val Ser Ala
            20

<210> SEQ ID NO 30
<211> LENGTH: 23
<212> TYPE: PRT
<213> ORGANISM: Mus musculus

<400> SEQUENCE: 30

Arg His Leu Gly Ser Gly Tyr Gly Trp Phe Ala Tyr Trp Gly Gln Gly
1               5                   10                  15

Thr Leu Val Thr Val Ser Ala
            20

<210> SEQ ID NO 31
<211> LENGTH: 23
<212> TYPE: PRT
<213> ORGANISM: Mus musculus

<400> SEQUENCE: 31

Arg His Leu Ile Ser Gly Tyr Gly Trp Phe Ala Tyr Trp Gly Gln Gly
1               5                   10                  15

Thr Leu Val Thr Val Ser Ala
            20

<210> SEQ ID NO 32
<211> LENGTH: 22
<212> TYPE: PRT
<213> ORGANISM: Rattus norvegicus

<400> SEQUENCE: 32

Ile Lys Glu Pro Arg Asp Trp Phe Phe Glu Phe Trp Gly Pro Gly Thr
1               5                   10                  15

Met Val Ser Val Ser Ser
            20
```

```
<210> SEQ ID NO 33
<211> LENGTH: 22
<212> TYPE: PRT
<213> ORGANISM: Rattus norvegicus

<400> SEQUENCE: 33

Ile Lys Glu Pro Arg Asp Trp Phe Phe Glu Phe Trp Gly Pro Gly Thr
1               5                   10                  15

Met Val Ser Val Ser Ser
            20

<210> SEQ ID NO 34
<211> LENGTH: 15
<212> TYPE: PRT
<213> ORGANISM: Mus musculus

<400> SEQUENCE: 34

Arg Ala Ser Glu Ser Val Asp Asn Tyr Gly Val Ser Phe Met Asn
1               5                   10                  15

<210> SEQ ID NO 35
<211> LENGTH: 16
<212> TYPE: PRT
<213> ORGANISM: Rattus norvegicus

<400> SEQUENCE: 35

Arg Ser Ser Gln Ser Leu Leu His Ser Asp Gly Asn Thr Phe Leu Ser
1               5                   10                  15

<210> SEQ ID NO 36
<211> LENGTH: 10
<212> TYPE: PRT
<213> ORGANISM: Mus musculus

<400> SEQUENCE: 36

Ser Ala Asn Ser Thr Val Asn Tyr Met Tyr
1               5                   10

<210> SEQ ID NO 37
<211> LENGTH: 12
<212> TYPE: PRT
<213> ORGANISM: Mus musculus

<400> SEQUENCE: 37

Thr Ala Ser Ser Ser Val Ser Ser Ser Tyr Phe His
1               5                   10

<210> SEQ ID NO 38
<211> LENGTH: 15
<212> TYPE: PRT
<213> ORGANISM: Mus musculus

<400> SEQUENCE: 38

Arg Ala Ser Glu Ser Val Asp Asn Tyr Gly Ile Ser Phe Met Asn
1               5                   10                  15

<210> SEQ ID NO 39
<211> LENGTH: 16
<212> TYPE: PRT
<213> ORGANISM: Mus musculus

<400> SEQUENCE: 39

Arg Ser Ser Gln Ser Leu Val His Ser Asp Gly Asn Thr Tyr Leu His
1               5                   10                  15
```

<210> SEQ ID NO 40
<211> LENGTH: 11
<212> TYPE: PRT
<213> ORGANISM: Mus musculus

<400> SEQUENCE: 40

Arg Ala Ser Gln Asp Ile Asn Asn Phe Leu Asn
1               5                   10

<210> SEQ ID NO 41
<211> LENGTH: 11
<212> TYPE: PRT
<213> ORGANISM: Mus musculus

<400> SEQUENCE: 41

Lys Ala Ser Gln Asp Val Asn Thr Ala Val Ala
1               5                   10

<210> SEQ ID NO 42
<211> LENGTH: 11
<212> TYPE: PRT
<213> ORGANISM: Mus musculus

<400> SEQUENCE: 42

Lys Ala Ser Gln Asp Val Ile Ser Ala Val Ala
1               5                   10

<210> SEQ ID NO 43
<211> LENGTH: 11
<212> TYPE: PRT
<213> ORGANISM: Rattus norvegicus

<400> SEQUENCE: 43

Arg Ala Ser Gln Gly Val Asn Asn Phe Leu Thr
1               5                   10

<210> SEQ ID NO 44
<211> LENGTH: 11
<212> TYPE: PRT
<213> ORGANISM: Rattus norvegicus

<400> SEQUENCE: 44

Arg Ala Ser Gln Gly Val Asn Asn Tyr Leu Thr
1               5                   10

<210> SEQ ID NO 45
<211> LENGTH: 7
<212> TYPE: PRT
<213> ORGANISM: Mus musculus

<400> SEQUENCE: 45

Ala Ala Ser Asn Gln Gly Ser
1               5

<210> SEQ ID NO 46
<211> LENGTH: 7
<212> TYPE: PRT
<213> ORGANISM: Rattus norvegicus

<400> SEQUENCE: 46

Leu Ala Ser Asn Arg Phe Ser
1               5

```
<210> SEQ ID NO 47
<211> LENGTH: 7
<212> TYPE: PRT
<213> ORGANISM: Mus musculus

<400> SEQUENCE: 47

Leu Thr Ser Asn Leu Ala Ser
1               5

<210> SEQ ID NO 48
<211> LENGTH: 7
<212> TYPE: PRT
<213> ORGANISM: Mus musculus

<400> SEQUENCE: 48

Ser Thr Ser Asn Leu Ala Ser
1               5

<210> SEQ ID NO 49
<211> LENGTH: 7
<212> TYPE: PRT
<213> ORGANISM: Mus musculus

<400> SEQUENCE: 49

Ala Ala Ser Asn Gln Gly Ser
1               5

<210> SEQ ID NO 50
<211> LENGTH: 7
<212> TYPE: PRT
<213> ORGANISM: Mus musculus

<400> SEQUENCE: 50

Lys Val Ser Lys Arg Phe Ser
1               5

<210> SEQ ID NO 51
<211> LENGTH: 7
<212> TYPE: PRT
<213> ORGANISM: Mus musculus

<400> SEQUENCE: 51

Tyr Thr Ser Lys Leu His Ser
1               5

<210> SEQ ID NO 52
<211> LENGTH: 7
<212> TYPE: PRT
<213> ORGANISM: Mus musculus

<400> SEQUENCE: 52

Trp Ala Ser Thr Arg His Thr
1               5

<210> SEQ ID NO 53
<211> LENGTH: 7
<212> TYPE: PRT
<213> ORGANISM: Mus musculus

<400> SEQUENCE: 53

Trp Ala Ser Thr Arg His Thr
1               5

<210> SEQ ID NO 54
<211> LENGTH: 7
```

```
<212> TYPE: PRT
<213> ORGANISM: Rattus norvegicus

<400> SEQUENCE: 54

Tyr Thr Ser Asn Leu Gln Ser
1               5

<210> SEQ ID NO 55
<211> LENGTH: 7
<212> TYPE: PRT
<213> ORGANISM: Rattus norvegicus

<400> SEQUENCE: 55

Tyr Thr Ser Asn Leu Gln Ser
1               5

<210> SEQ ID NO 56
<211> LENGTH: 9
<212> TYPE: PRT
<213> ORGANISM: Mus musculus

<400> SEQUENCE: 56

Gln Gln Thr Lys Glu Val Thr Trp Thr
1               5

<210> SEQ ID NO 57
<211> LENGTH: 9
<212> TYPE: PRT
<213> ORGANISM: Rattus norvegicus

<400> SEQUENCE: 57

Phe Gln His Thr His Leu Pro Leu Thr
1               5

<210> SEQ ID NO 58
<211> LENGTH: 9
<212> TYPE: PRT
<213> ORGANISM: Mus musculus

<400> SEQUENCE: 58

Gln Gln Trp Asn Ser Asn Pro Pro Thr
1               5

<210> SEQ ID NO 59
<211> LENGTH: 9
<212> TYPE: PRT
<213> ORGANISM: Mus musculus

<400> SEQUENCE: 59

His Gln Tyr His Arg Ser Pro Arg Thr
1               5

<210> SEQ ID NO 60
<211> LENGTH: 9
<212> TYPE: PRT
<213> ORGANISM: Mus musculus

<400> SEQUENCE: 60

Gln Gln Ser Lys Glu Val Pro Phe Thr
1               5

<210> SEQ ID NO 61
<211> LENGTH: 9
<212> TYPE: PRT
<213> ORGANISM: Mus musculus
```

<400> SEQUENCE: 61

Ser Gln Ser Thr His Val Pro Pro Thr
1               5

<210> SEQ ID NO 62
<211> LENGTH: 9
<212> TYPE: PRT
<213> ORGANISM: Mus musculus

<400> SEQUENCE: 62

Gln Gln Gly His Thr Leu Pro Pro Thr
1               5

<210> SEQ ID NO 63
<211> LENGTH: 10
<212> TYPE: PRT
<213> ORGANISM: Mus musculus

<400> SEQUENCE: 63

Gln Gln His Ser Tyr Thr Pro Pro Trp Thr
1               5                   10

<210> SEQ ID NO 64
<211> LENGTH: 10
<212> TYPE: PRT
<213> ORGANISM: Mus musculus

<400> SEQUENCE: 64

Gln Gln His Ser Tyr Thr Pro Pro Trp Thr
1               5                   10

<210> SEQ ID NO 65
<211> LENGTH: 9
<212> TYPE: PRT
<213> ORGANISM: Rattus norvegicus

<400> SEQUENCE: 65

Gln Gln Tyr His Gly Phe Pro Asn Thr
1               5

<210> SEQ ID NO 66
<211> LENGTH: 9
<212> TYPE: PRT
<213> ORGANISM: Rattus norvegicus

<400> SEQUENCE: 66

Gln Gln Tyr His Gly Phe Pro Asn Thr
1               5

<210> SEQ ID NO 67
<211> LENGTH: 122
<212> TYPE: PRT
<213> ORGANISM: Artificial Sequence
<220> FEATURE:
<223> OTHER INFORMATION: humanized antibody sequence
<220> FEATURE:
<221> NAME/KEY: VARIANT
<222> LOCATION: (24)..(24)
<223> OTHER INFORMATION: Can be A or F
<220> FEATURE:
<221> NAME/KEY: VARIANT
<222> LOCATION: (69)..(69)
<223> OTHER INFORMATION: Can be F or L
<220> FEATURE:
<221> NAME/KEY: VARIANT
<222> LOCATION: (73)..(73)

```
<223> OTHER INFORMATION: Can be R or K
<220> FEATURE:
<221> NAME/KEY: VARIANT
<222> LOCATION: (75)..(75)
<223> OTHER INFORMATION: Can be N or T
<220> FEATURE:
<221> NAME/KEY: VARIANT
<222> LOCATION: (80)..(80)
<223> OTHER INFORMATION: Can be L or V
<220> FEATURE:
<221> NAME/KEY: VARIANT
<222> LOCATION: (98)..(98)
<223> OTHER INFORMATION: Can be A or V

<400> SEQUENCE: 67

Gln Val Gln Leu Val Glu Ser Gly Gly Val Val Gln Pro Gly Arg
1               5                   10                  15

Ser Leu Arg Leu Ser Cys Ala Xaa Ser Gly Phe Ser Leu Ser Thr Ser
            20                  25                  30

Gly Met Gly Val Gly Trp Val Arg Gln Ala Pro Gly Lys Gly Leu Glu
        35                  40                  45

Trp Val Ala His Ile Trp Trp Asp Asp Lys Tyr Tyr Ser Pro Ser
    50                  55                  60

Leu Lys Ser Arg Xaa Thr Ile Ser Xaa Asp Xaa Ser Lys Asn Thr Xaa
65                  70                  75                  80

Tyr Leu Gln Met Asn Ser Leu Arg Ala Glu Asp Thr Ala Val Tyr Tyr
                85                  90                  95

Cys Xaa Arg Ser Tyr Tyr Tyr Gly Ser Ser Gly Ala Met Asp Tyr Trp
            100                 105                 110

Gly Gln Gly Thr Leu Val Thr Val Ser Ser
        115                 120

<210> SEQ ID NO 68
<211> LENGTH: 113
<212> TYPE: PRT
<213> ORGANISM: Artificial Sequence
<220> FEATURE:
<223> OTHER INFORMATION: Humanized antibody sequence

<400> SEQUENCE: 68

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Val Glu Ile Lys
            100                 105                 110

Arg

<210> SEQ ID NO 69
<211> LENGTH: 123
<212> TYPE: PRT
<213> ORGANISM: Artificial Sequence
<220> FEATURE:
```

<223> OTHER INFORMATION: Humanized antibody sequence
<220> FEATURE:
<221> NAME/KEY: VARIANT
<222> LOCATION: (97)..(97)
<223> OTHER INFORMATION: Can be A or T
<220> FEATURE:
<221> NAME/KEY: VARIANT
<222> LOCATION: (98)..(98)
<223> OTHER INFORMATION: Can be R or T

<400> SEQUENCE: 69

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Tyr Ile His Ala Asn Gly Gly Ser Thr Tyr Tyr Arg Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Xaa Xaa Gly Ser Phe Met Tyr Ala Ala Asp Tyr Tyr Ile Met Asp Ala
            100                 105                 110

Trp Gly Gln Gly Thr Leu Val Thr Val Ser Ser
            115                 120

<210> SEQ ID NO 70
<211> LENGTH: 113
<212> TYPE: PRT
<213> ORGANISM: Artificial Sequence
<220> FEATURE:
<223> OTHER INFORMATION: Humanized antibody sequence

<400> SEQUENCE: 70

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Asn Thr Phe Leu Ser Trp Tyr Leu Gln Lys Pro Gly Gln Ser
        35                  40                  45

Pro Gln Leu Leu Ile Tyr Leu Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln His
                85                  90                  95

Thr His Leu Pro Leu Thr Phe Gly Gln Gly Thr Lys Val Glu Ile Lys
            100                 105                 110

Arg

<210> SEQ ID NO 71
<211> LENGTH: 118
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (48)..(48)

<223> OTHER INFORMATION: Can be M or I
<220> FEATURE:
<221> NAME/KEY: VARIANT
<222> LOCATION: (68)..(68)
<223> OTHER INFORMATION: Can be V or A
<220> FEATURE:
<221> NAME/KEY: VARIANT
<222> LOCATION: (70)..(70)
<223> OTHER INFORMATION: Can be M or F
<220> FEATURE:
<221> NAME/KEY: VARIANT
<222> LOCATION: (72)..(72)
<223> OTHER INFORMATION: Can be T or A

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Arg Tyr
            20                  25                  30

Trp Ile Glu Trp Val Arg Gln Ala Pro Gly Gln Gly Leu Glu Trp Xaa
        35                  40                  45

Gly Glu Ile Leu Pro Gly Ser Gly Ser Ser Asn Tyr Asn Glu Lys Phe
    50                  55                  60

Lys Asp Arg Xaa Thr Xaa Thr Xaa Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Val Tyr Tyr Tyr Ala Met Asp Phe Trp Gly Gln Gly Thr
            100                 105                 110

Leu Val Thr Val Ser Ser
        115

<210> SEQ ID NO 72
<211> LENGTH: 109
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (48)..(48)
<223> OTHER INFORMATION: Can be L or W
<220> FEATURE:
<221> NAME/KEY: VARIANT
<222> LOCATION: (72)..(72)
<223> OTHER INFORMATION: Can be F or Y

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Phe His Trp Tyr Gln Gln Lys Pro Gly Gln Ala Pro Arg Leu Xaa
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Xaa Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Arg Thr Phe Gly Gln Gly Thr Lys Val Glu Ile Lys Arg
            100                 105

```
<210> SEQ ID NO 73
<211> LENGTH: 121
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (24)..(24)
<223> OTHER INFORMATION: Can be V or F
<220> FEATURE:
<221> NAME/KEY: VARIANT
<222> LOCATION: (50)..(50)
<223> OTHER INFORMATION: Can be I or L
<220> FEATURE:
<221> NAME/KEY: VARIANT
<222> LOCATION: (51)..(51)
<223> OTHER INFORMATION: Can be G or A
<220> FEATURE:
<221> NAME/KEY: VARIANT
<222> LOCATION: (69)..(69)
<223> OTHER INFORMATION: Can be V or L
<220> FEATURE:
<221> NAME/KEY: VARIANT
<222> LOCATION: (71)..(71)
<223> OTHER INFORMATION: Can be I or V
<220> FEATURE:
<221> NAME/KEY: VARIANT
<222> LOCATION: (73)..(73)
<223> OTHER INFORMATION: Can be V or K
<220> FEATURE:
<221> NAME/KEY: VARIANT
<222> LOCATION: (80)..(80)
<223> OTHER INFORMATION: Can be F or A
<220> FEATURE:
<221> NAME/KEY: VARIANT
<222> LOCATION: (99)..(99)
<223> OTHER INFORMATION: Can be R or Q

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Xaa Ser Gly Phe Ser Leu Ser Thr Tyr
                20                  25                  30

Gly Val Gly Val Gly Trp Ile Arg Gln Pro Pro Gly Lys Gly Leu Glu
            35                  40                  45

Trp Xaa Xaa Asn Ile Trp Trp Asp Asp Asn Tyr Tyr Asn Pro Ser
        50                  55                  60

Leu Ile His Arg Xaa Thr Xaa Ser Xaa Asp Thr Ser Lys Asn Gln Xaa
65                  70                  75                  80

Ser Leu Lys Leu Ser Ser Val Thr Ala Ala Asp Thr Ala Val Tyr Tyr
                85                  90                  95

Cys Ala Xaa Ile Lys Glu Pro Arg Asp Trp Phe Phe Glu Phe Trp Gly
            100                 105                 110

Gln Gly Thr Leu Val Thr Val Ser Ser
            115                 120

<210> SEQ ID NO 74
<211> LENGTH: 108
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (46)..(46)
<223> OTHER INFORMATION: Can be L or P
<220> FEATURE:
<221> NAME/KEY: VARIANT
```

```
<222> LOCATION: (49)..(49)
<223> OTHER INFORMATION: Can be Y or F
<220> FEATURE:
<221> NAME/KEY: VARIANT
<222> LOCATION: (71)..(71)
<223> OTHER INFORMATION: Can be F or Y

<400> SEQUENCE: 74
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Asn Asn Phe
            20                  25                  30

Leu Thr Trp Tyr Gln Gln Lys Pro Gly Lys Ala Pro Lys Xaa Leu Ile
        35                  40                  45

Xaa Tyr Thr Ser Asn Leu Gln Ser Gly Val Pro Ser Arg Phe Ser Gly
    50                  55                  60

Ser Gly Ser Gly Thr Asp Xaa Thr Leu Thr Ile Ser Ser Leu Gln Pro
65              70                  75                  80

Glu Asp Phe Ala Thr Tyr Tyr Cys Gln Gln Tyr His Gly Phe Pro Asn
                85                  90                  95

Thr Phe Gly Gln Gly Thr Lys Val Glu Ile Lys Arg
            100                 105

```
<210> SEQ ID NO 75
<211> LENGTH: 121
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (24)..(24)
<223> OTHER INFORMATION: Can be V or F
<220> FEATURE:
<221> NAME/KEY: VARIANT
<222> LOCATION: (50)..(50)
<223> OTHER INFORMATION: Can be I or L
<220> FEATURE:
<221> NAME/KEY: VARIANT
<222> LOCATION: (51)..(51)
<223> OTHER INFORMATION: Can be G or A
<220> FEATURE:
<221> NAME/KEY: VARIANT
<222> LOCATION: (69)..(69)
<223> OTHER INFORMATION: Can be V or L
<220> FEATURE:
<221> NAME/KEY: VARIANT
<222> LOCATION: (73)..(73)
<223> OTHER INFORMATION: Can be V or K
<220> FEATURE:
<221> NAME/KEY: VARIANT
<222> LOCATION: (80)..(80)
<223> OTHER INFORMATION: Can be F or A
<220> FEATURE:
<221> NAME/KEY: VARIANT
<222> LOCATION: (99)..(99)
<223> OTHER INFORMATION: Can be R or Q

<400> SEQUENCE: 75
```

Gln Val Gln Leu Gln Glu Ser Gly Pro Gly Leu Val Lys Pro Ser Glu
1               5                   10                  15

Thr Leu Ser Leu Thr Cys Thr Xaa Ser Gly Phe Ser Leu Ser Thr Tyr
            20                  25                  30

Gly Val Gly Val Gly Trp Ile Arg Gln Pro Pro Gly Lys Gly Leu Glu
        35                  40                  45

Trp Xaa Xaa Asn Ile Trp Trp Asp Asp Lys Tyr Tyr Asn Pro Ser
    50                  55                  60

```
Leu Lys Asn Arg Xaa Thr Ile Ser Xaa Asp Thr Ser Lys Asn Gln Xaa
 65                  70                  75                  80

Ser Leu Lys Leu Ser Ser Val Thr Ala Ala Asp Thr Ala Val Tyr Tyr
                 85                  90                  95

Cys Ala Xaa Ile Lys Glu Pro Arg Asp Trp Phe Phe Glu Phe Trp Gly
            100                 105                 110

Gln Gly Thr Leu Val Thr Val Ser Ser
            115                 120
```

```
<210> SEQ ID NO 76
<211> LENGTH: 108
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (46)..(46)
<223> OTHER INFORMATION: Can be L or P
<220> FEATURE:
<221> NAME/KEY: VARIANT
<222> LOCATION: (49)..(49)
<223> OTHER INFORMATION: Can be Y or F
<220> FEATURE:
<221> NAME/KEY: VARIANT
<222> LOCATION: (71)..(71)
<223> OTHER INFORMATION: Can be F or Y

<400> SEQUENCE: 76

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Val Asn Asn Tyr
             20                  25                  30

Leu Thr Trp Tyr Gln Gln Lys Pro Gly Lys Ala Pro Lys Xaa Leu Ile
         35                  40                  45

Xaa Tyr Thr Ser Asn Leu Gln Ser Gly Val Pro Ser Arg Phe Ser Gly
 50                  55                  60

Ser Gly Ser Gly Thr Asp Xaa Thr Leu Thr Ile Ser Ser Leu Gln Pro
 65                  70                  75                  80

Glu Asp Phe Ala Thr Tyr Tyr Cys Gln Gln Tyr His Gly Phe Pro Asn
                 85                  90                  95

Thr Phe Gly Gln Gly Thr Lys Val Glu Ile Lys Arg
            100                 105
```

```
<210> SEQ ID NO 77
<211> LENGTH: 117
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (96)..(96)
<223> OTHER INFORMATION: Can be A or Q

<400> SEQUENCE: 77

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Val Arg Asn Tyr
             20                  25                  30

Ala Met Ser Trp Val Arg Gln Ala Pro Gly Lys Gly Leu Glu Trp Val
         35                  40                  45
```

```
Ala Ser Ile Ser Thr Gly Asp Arg Ser Tyr Leu Pro Asp Ser Met Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Xaa
                85                  90                  95

Arg Tyr Phe Asp Phe Asp Ser Phe Ala Phe Trp Gly Gln Gly Thr Leu
            100                 105                 110

Val Thr Val Ser Ser
        115
```

<210> SEQ ID NO 78
<211> LENGTH: 108
<212> TYPE: PRT
<213> ORGANISM: Artificial Sequence
<220> FEATURE:
<223> OTHER INFORMATION: Humanized antibody sequence

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg
            100                 105
```

<210> SEQ ID NO 79
<211> LENGTH: 120
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (47)..(47)
<223> OTHER INFORMATION: Can be W or Y
<220> FEATURE:
<221> NAME/KEY: VARIANT
<222> LOCATION: (48)..(48)
<223> OTHER INFORMATION: Can be I or M
<220> FEATURE:
<221> NAME/KEY: VARIANT
<222> LOCATION: (71)..(71)
<223> OTHER INFORMATION: Can be V or R
<220> FEATURE:
<221> NAME/KEY: VARIANT
<222> LOCATION: (96)..(96)
<223> OTHER INFORMATION: Can be A or S

<400> SEQUENCE: 79

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Xaa Xaa
```

```
                35                  40                  45

Gly Tyr Ile Ser Tyr Ser Gly Ser Thr Tyr Tyr Asn Pro Ser Leu Arg
        50                  55                  60

Gly Arg Val Thr Ile Ser Xaa Asp Thr Ser Lys Asn Gln Phe Ser Leu
65                  70                  75                  80

Lys Leu Ser Ser Val Thr Ala Ala Asp Thr Ala Val Tyr Tyr Cys Xaa
                85                  90                  95

Arg Arg His Leu Gly Ser Gly Tyr Gly Trp Phe Ala Tyr Trp Gly Gln
            100                 105                 110

Gly Thr Leu Val Thr Val Ser Ser
            115                 120

<210> SEQ ID NO 80
<211> LENGTH: 109
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (71)..(71)
<223> OTHER INFORMATION: Can be F or Y

<400> SEQUENCE: 80

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Asn Thr Ala
                20                  25                  30

Val Ala Trp Tyr Gln Gln Lys Pro Gly Gln Pro Pro Lys Leu Leu Ile
            35                  40                  45

Tyr Trp Ala Ser Thr Arg His Thr Gly Val Pro Asp Arg Phe Ser Gly
        50                  55                  60

Ser Gly Ser Gly Thr Asp Xaa Thr Leu Thr Ile Ser Ser Leu Gln Ala
65                  70                  75                  80

Glu Asp Val Ala Val Tyr Tyr Cys Gln Gln His Ser Tyr Thr Pro Pro
                85                  90                  95

Trp Thr Phe Gly Gln Gly Thr Lys Val Glu Ile Lys Arg
            100                 105

<210> SEQ ID NO 81
<211> LENGTH: 118
<212> TYPE: PRT
<213> ORGANISM: Artificial Sequence
<220> FEATURE:
<223> OTHER INFORMATION: Humanized antibody sequence

<400> SEQUENCE: 81

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Ser Ile Ser Ser Gly Gly Thr Thr Tyr Tyr Pro Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

-continued

Arg Val Gly Gly Tyr Tyr Asp Ser Met Asp Tyr Trp Gly Gln Gly Thr
            100                 105                 110

Leu Val Thr Val Ser Ser
        115

<210> SEQ ID NO 82
<211> LENGTH: 112
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (31)..(31)
<223> OTHER INFORMATION: Can be N or Q
<220> FEATURE:
<221> NAME/KEY: VARIANT
<222> LOCATION: (57)..(57)
<223> OTHER INFORMATION: Can be N or Q

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Xaa Tyr
            20                  25                  30

Gly Val Ser Phe Met Asn Trp Tyr Gln Gln Lys Pro Gly Gln Ala Pro
        35                  40                  45

Arg Leu Leu Ile Tyr Ala Ala Ser Xaa Gln Gly Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Thr Lys
                85                  90                  95

Glu Val Thr Trp Thr Phe Gly Gln Gly Thr Lys Val Glu Ile Lys Arg
            100                 105                 110

<210> SEQ ID NO 83
<211> LENGTH: 120
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (47)..(47)
<223> OTHER INFORMATION: Can be W or Y
<220> FEATURE:
<221> NAME/KEY: VARIANT
<222> LOCATION: (48)..(48)
<223> OTHER INFORMATION: Can be I or M
<220> FEATURE:
<221> NAME/KEY: VARIANT
<222> LOCATION: (67)..(67)
<223> OTHER INFORMATION: Can be V or I
<220> FEATURE:
<221> NAME/KEY: VARIANT
<222> LOCATION: (71)..(71)
<223> OTHER INFORMATION: Can be V or R
<220> FEATURE:
<221> NAME/KEY: VARIANT
<222> LOCATION: (78)..(78)
<223> OTHER INFORMATION: Can be F or Y
<220> FEATURE:
<221> NAME/KEY: VARIANT
<222> LOCATION: (96)..(96)
<223> OTHER INFORMATION: Can be A or S

<400> SEQUENCE: 83

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Xaa Xaa
            35                  40                  45

Gly Phe Ile Ser Tyr Ser Gly Asn Thr Tyr Tyr Asn Pro Ser Leu Arg
    50                  55                  60

Ser Arg Xaa Thr Ile Ser Xaa Asp Thr Ser Lys Asn Gln Xaa Ser Leu
65              70                  75                  80

Lys Leu Ser Ser Val Thr Ala Ala Asp Thr Ala Val Tyr Tyr Cys Xaa
            85                  90                  95

Arg Arg His Leu Ile Ser Gly Tyr Gly Trp Phe Ala Tyr Trp Gly Gln
            100                 105                 110

Gly Thr Leu Val Thr Val Ser Ser
            115                 120

<210> SEQ ID NO 84
<211> LENGTH: 109
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (1)..(1)
<223> OTHER INFORMATION: Can be D or V

<400> SEQUENCE: 84

Xaa Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ile Ser Ala
            20                  25                  30

Val Ala Trp Tyr Gln Gln Lys Pro Gly Gln Pro Pro Lys Leu Leu Ile
            35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65              70                  75                  80

Glu Asp Val Ala Val Tyr Tyr Cys Gln Gln His Ser Tyr Thr Pro Pro
            85                  90                  95

Trp Thr Phe Gly Gln Gly Thr Lys Val Glu Ile Lys Arg
            100                 105

<210> SEQ ID NO 85
<211> LENGTH: 119
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (48)..(48)
<223> OTHER INFORMATION: Can be M or I
<220> FEATURE:
<221> NAME/KEY: VARIANT
<222> LOCATION: (68)..(68)
<223> OTHER INFORMATION: Can be V or A
<220> FEATURE:
<221> NAME/KEY: VARIANT
<222> LOCATION: (70)..(70)
<223> OTHER INFORMATION: Can be M or L

```
<220> FEATURE:
<221> NAME/KEY: VARIANT
<222> LOCATION: (72)..(72)
<223> OTHER INFORMATION: Can be T or A
<220> FEATURE:
<221> NAME/KEY: VARIANT
<222> LOCATION: (74)..(74)
<223> OTHER INFORMATION: Can be T or K

<400> SEQUENCE: 85
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Xaa
        35                  40                  45

Gly Tyr Ile Asn Pro Arg Ser Val Tyr Thr Asn Tyr Asn Gln Lys Phe
    50                  55                  60

Lys Asp Arg Xaa Thr Xaa Thr Xaa Asp Xaa Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Leu Gly Gly Tyr Tyr Asp Thr Met Asp Tyr Trp Gly Gln Gly
            100                 105                 110

Thr Leu Val Thr Val Ser Ser
        115

```
<210> SEQ ID NO 86
<211> LENGTH: 112
<212> TYPE: PRT
<213> ORGANISM: Artificial Sequence
<220> FEATURE:
<223> OTHER INFORMATION: Humanized antibody sequence

<400> SEQUENCE: 86
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Tyr Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Lys
                85                  90                  95

Glu Val Pro Phe Thr Phe Gly Gln Gly Thr Lys Val Glu Ile Lys Arg
            100                 105                 110

```
<210> SEQ ID NO 87
<211> LENGTH: 118
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (49)..(49)
<223> OTHER INFORMATION: Can be I or M
<220> FEATURE:
<221> NAME/KEY: VARIANT
```

<222> LOCATION: (68)..(68)
<223> OTHER INFORMATION: Can be V or I
<220> FEATURE:
<221> NAME/KEY: VARIANT
<222> LOCATION: (72)..(72)
<223> OTHER INFORMATION: Can be V or R

<400> SEQUENCE: 87

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Tyr Ser Ile Thr Ser Asp
            20                  25                  30
Tyr Ala Trp Asn Trp Ile Arg Gln Pro Pro Gly Lys Gly Leu Glu Trp
        35                  40                  45
Xaa Gly Tyr Ile Ser Tyr Ser Gly Ser Thr Arg Tyr Asn Pro Ser Leu
    50                  55                  60
Lys Ser Arg Xaa Thr Ile Ser Xaa Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gln Leu Gly Leu Arg Phe Phe Asp Tyr Trp Gly Gln Gly Thr
            100                 105                 110
Leu Val Thr Val Ser Ser
            115
```

<210> SEQ ID NO 88
<211> LENGTH: 107
<212> TYPE: PRT
<213> ORGANISM: Artificial Sequence
<220> FEATURE:
<223> OTHER INFORMATION: Humanized antibody sequence
<220> FEATURE:
<221> NAME/KEY: VARIANT
<222> LOCATION: (45)..(45)
<223> OTHER INFORMATION: Can be L or P
<220> FEATURE:
<221> NAME/KEY: VARIANT
<222> LOCATION: (46)..(46)
<223> OTHER INFORMATION: Can be L or C

<400> SEQUENCE: 88

```
Glu Ile Val Leu Thr Gln Ser Pro Gly Thr Leu Ser Leu Ser Pro Gly
1               5                   10                  15
Glu Arg Ala Thr Leu Ser Cys Ser Ala Asn Ser Thr Val Asn Tyr Met
            20                  25                  30
Tyr Trp Tyr Gln Gln Lys Pro Gly Gln Ala Pro Arg Xaa Xaa Ile Tyr
        35                  40                  45
Leu Thr Ser Asn Leu Ala Ser Gly Ile Pro Asp Arg Phe Ser Gly Ser
    50                  55                  60
Gly Ser Gly Thr Asp Phe Thr Leu Thr Ile Ser Arg Leu Glu Pro Glu
65                  70                  75                  80
Asp Phe Ala Val Tyr Tyr Cys Gln Gln Trp Asn Ser Asn Pro Pro Thr
                85                  90                  95
Phe Gly Gln Gly Thr Lys Val Glu Ile Lys Arg
            100                 105
```

MODULATION OF TUMOR IMMUNITY

CROSS-REFERENCE TO RELATED APPLICATIONS

This application is a divisional application of U.S. application Ser. No. 14/912,733, filed on Feb. 18, 2016, which is a § 371 National Stage Application of PCT/US2014/051402, filed on Aug. 18, 2014, which claims the benefit of priority to U.S. Provisional Application No. 61/867,976, filed Aug. 20, 2013, the disclosure of which are incorporated by reference herein in their entireties.

FIELD OF THE INVENTION

The present invention relates to modulation of tumor immunity in the treatment of advanced tumors. In particular, the present invention provides antagonists of PD-1 in combination with agonists of GITR to enhance anti-tumor responses to advanced tumors.

BACKGROUND OF THE INVENTION

The tumor microenvironment is an important aspect of cancer biology that contributes to tumor initiation, tumor progression and responses to therapy. Cells and molecules of the immune system are a fundamental component of the tumor microenvironment. Importantly, therapeutic strategies can harness the immune system to specifically target tumor cells and this is particularly appealing owing to the possibility of inducing tumor-specific immunological memory, which might cause long-lasting regression and prevent relapse in cancer patients.

The composition and characteristics of the tumor microenvironment vary widely and are important in determining the anti-tumor immune response. For example, certain cells of the immune system, including natural killer cells, dendritic cells (DCs) and effector T cells, are capable of driving potent anti-tumor responses. However, tumor cells often induce an immunosuppressive microenvironment, which favors the development of immunosuppressive populations of immune cells, such as myeloid-derived suppressor cells and regulatory T cells. Understanding the complexity of immunomodulation by tumors is important for the development of immunotherapy. Various strategies are being developed to enhance anti-tumor immune responses, including DC-based vaccines and antagonists of inhibitory signaling pathways to overcome 'immune checkpoints'.

Glucocorticoid-induced TNFR-related protein (GITR), a member of the TNFR superfamily, is expressed in many components of the innate and adaptive immune system (see, e.g., Hanabuchi, et al. (2006) *Blood* 107:3617-3623; and Nocentini and Riccardi (2005) *Eur. J. Immunol.* 2005. 35:1016-1022). Its membrane expression is increased following T cell activation (Hanabuchi, supra; and Nocentini and Riccardi, supra); its triggering co-activates effector T lymphocytes and modulates regulatory T cell (Treg) activity (see, e.g., McHugh, et al. (2002) *Immunity* 2002. 16:311-323; Shimizu, et al. (2002) *Nat. Immunol.* 3:135-142; Ronchetti, et al. (2004) *Eur. J. Immunol.* 34:613-622; and Tone, et al. (2003) *Proc. Natl. Acad. Sci. USA* 100:15059-15064).

GITR is activated by GITR ligand (GITRL), which is mainly expressed on APC and has been suggested to deliver signals by its cytoplasmic domain, although further studies are necessary to define the biochemical signaling (Nocentini, supra; Ronchetti, supra; Suvas, et al. (2005) *J. Virol.* 79:11935-11942; and Shin, et al. (2002) *Cytokine* 19:187-192).

GITR activation increases resistance to tumors and viral infections, is involved in autoimmune/inflammatory processes and regulates leukocyte extravasation (Nocentini supra; Cuzzocrea, et al. (2004) *J. Leukoc. Biol.* 76:933-940; Shevach, et al. (2006) *Nat. Rev. Immunol.* 6:613-618; Cuzzocrea, et al. (2006) *J. Immunol.* 177:631-641; and Cuzzocrea, et al. (2007) *FASEB J.* 21:117-129). In tumor mouse models, agonist GITR antibody, DTA-1, was combined with an antagonist CTLA-4 antibody, and showed synergistic results in complete tumor regression of advanced stage tumors in some test group mice (Ko, et al. (2005) *J. Exp. Med.* 7:885-891).

Programmed death receptor 1 (PD-1) is an immunoinhibitory receptor that is primarily expressed on activated T and B cells. Interaction with its ligands has been shown to attenuate T-cell responses both in vitro and in vivo. Blockade of the interaction between PD-1 and one of its ligands, PD-L1, has been shown to enhance tumor-specific CD8+ T-cell immunity and may therefore be helpful in clearance of tumor cells by the immune system.

PD-1 (encoded by the gene Pdcd1) is an Immunoglobulin superfamily member related to CD28, and CTLA-4. PD-1 has been shown to negatively regulate antigen receptor signaling upon engagement of its ligands (PD-L1 and/or PD-L2) The structure of murine PD-1 has been solved as well as the co-crystal structure of mouse PD-1 with human PD-L1 (Zhang, X., et al., (2004) *Immunity* 20: 337-347; Lin, et al., (2008) *Proc. Natl. Acad. Sci. USA* 105: 3011-6). PD-1 and like family members are type I transmembrane glycoproteins containing an Ig Variable-type (V-type) domain responsible for ligand binding and a cytoplasmic tail that is responsible for the binding of signaling molecules. The cytoplasmic tail of PD-1 contains two tyrosine-based signaling motifs, an ITIM (immunoreceptor tyrosine-based inhibition motif) and an ITSM (immunoreceptor tyrosine-based switch motif).

In humans, expression of PD-1 (on tumor infiltrating lymphocytes) and/or PD-L1 (on tumor cells) has been found in a number of primary tumor biopsies assessed by immunohistochemistry. Such tissues include cancers of the lung, liver, ovary, cervix, skin, colon, glioma, bladder, breast, kidney, esophagus, stomach, oral squamous cell, urothelial cell, and pancreas as well as tumors of the head and neck (Brown, J. A., et al., (2003) *J. Immunol.* 170: 1257-1266; Dong H., et al., (2002) *Nat. Med.* 8: 793-800; Wintterle, et al., (2003) *Cancer Res.* 63: 7462-7467; Strome, S. E., et al., (2003) *Cancer Res.* 63: 6501-6505; Thompson, R. H., et al., (2006) *Cancer Res.* 66: 3381-5; Thompson, et al., (2007) *Clin. Cancer Res.* 13: 1757-61; Nomi, T., et al., (2007) *Clin. Cancer Res.* 13: 2151-7). More strikingly, PD-ligand expression on tumor cells has been correlated to poor prognosis of cancer patients across multiple tumor types (reviewed in Okazaki and Honjo, (2007) *Int. Immunol.* 19: 813-824).

To date, numerous studies have shown that interaction of PD-1 with its ligands (PD-L1 and PD-L2) leads to the inhibition of lymphocyte proliferation in vitro and in vivo. Blockade of the PD-1/PD-L1 interaction could lead to enhanced tumor-specific T-cell immunity and therefore be helpful in clearance of tumor cells by the immune system. To address this issue, a number of studies were performed. In a murine model of aggressive pancreatic cancer (Nomi, T., et al. (2007) *Clin. Cancer Res.* 13: 2151-2157), the therapeutic efficacy of PD-1/PD-L1 blockade was demonstrated. Administration of either PD-1 or PD-L1 directed antibody significantly inhibited tumor growth. Antibody blockade effectively promoted tumor reactive CD8+ T cell infiltration into the tumor resulting in the up-regulation of anti-tumor effectors including IFN gamma, granzyme B and perforin. Additionally, the authors showed that PD-1 blockade can be effectively combined with chemotherapy to yield a synergistic effect. In another study, using a model of squamous cell carcinoma in mice, antibody blockade of PD-1 or PD-L1 significantly inhibited tumor growth (Tsushima, F., et al., (2006) *Oral Oncol.* 42: 268-274).

The need exists for improved methods and compositions for the treatment of immune and proliferative disorders, e.g., tumors and cancers, by use of agents that modulate tumor immunity. The present invention fills this need by providing antagonists of PD-1 in combination with agonists of GITR to treat advanced stage tumors.

SUMMARY OF THE INVENTION

Figure 1A:
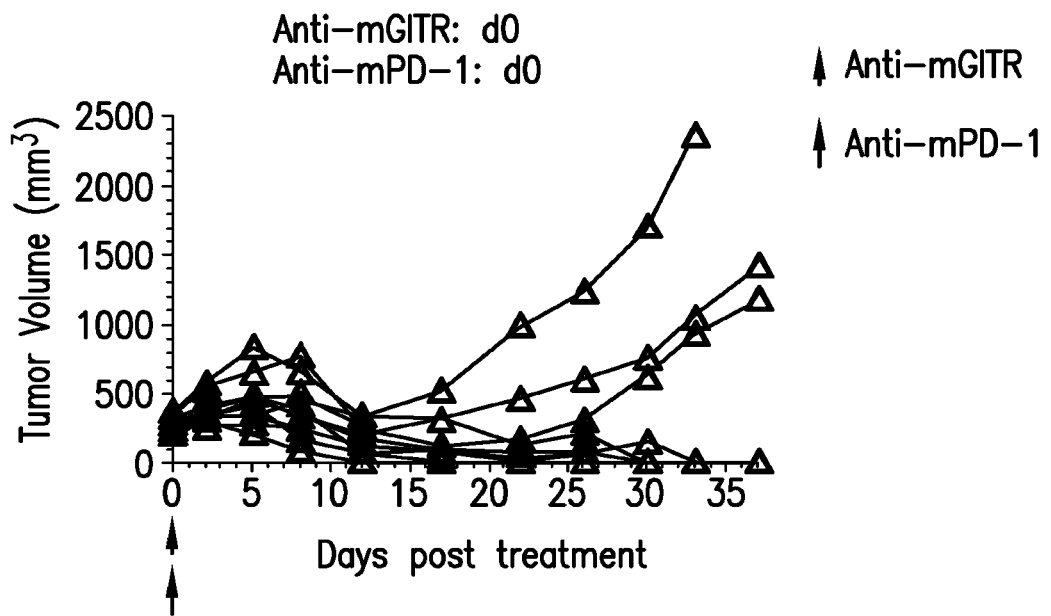
FIGS. 1A-1K shows the effect of anti-GITR antibodies dosed alone or in combination with anti-PD-1 antibodies on the anti-tumor response of mice implanted with MC38 cell line (n=10/group). Treatment was commenced when tumors reached 240-360 mm$^3$.
Figure 1B:
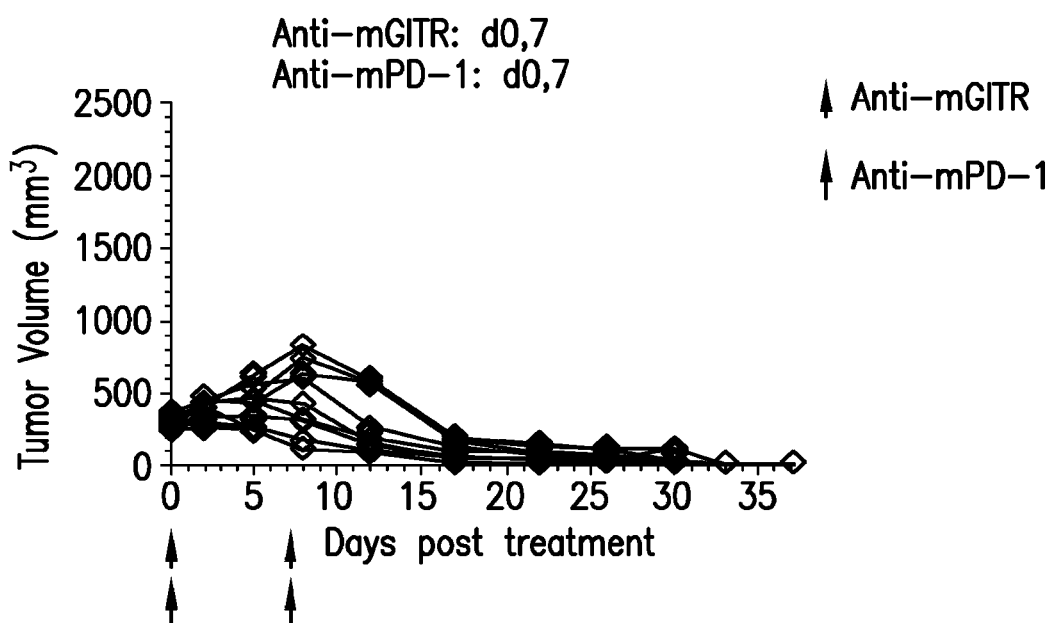
Figure 1C:
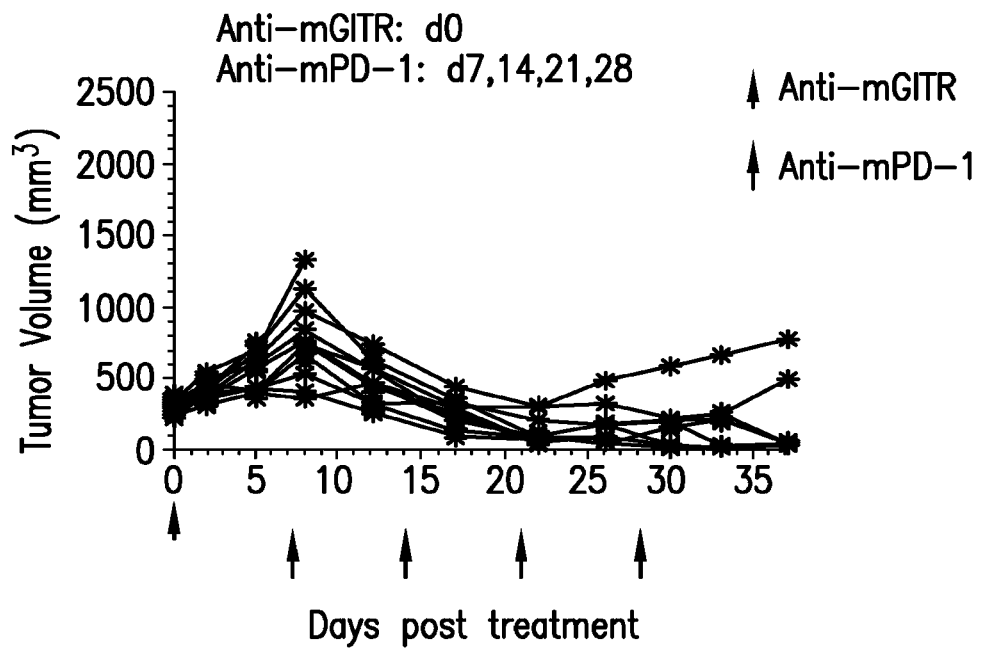
Figure 1D:
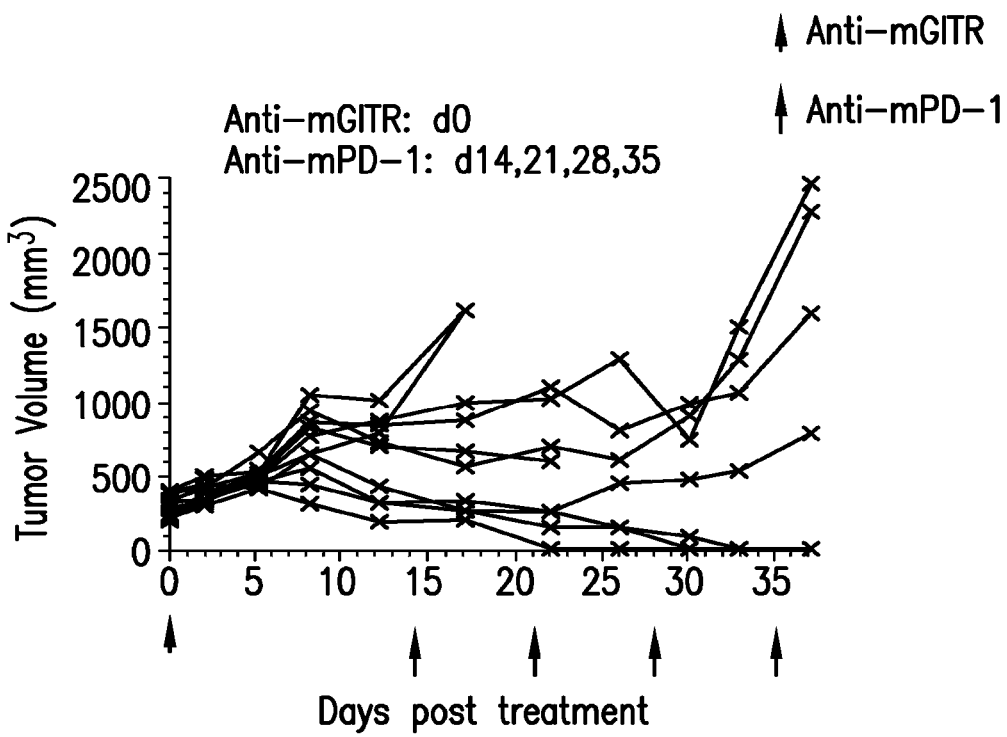
Figure 1E:
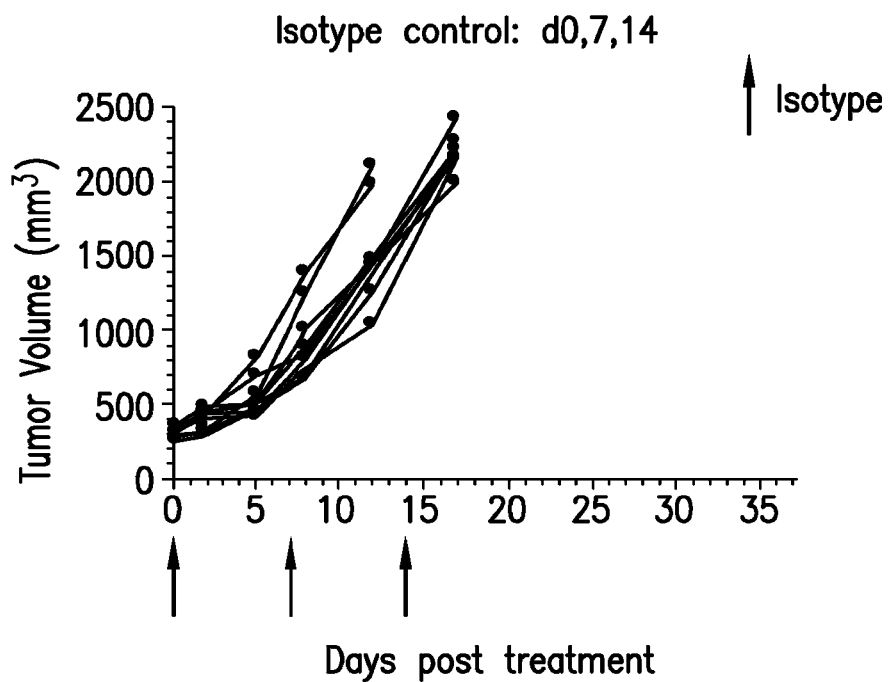
Figure 1F:
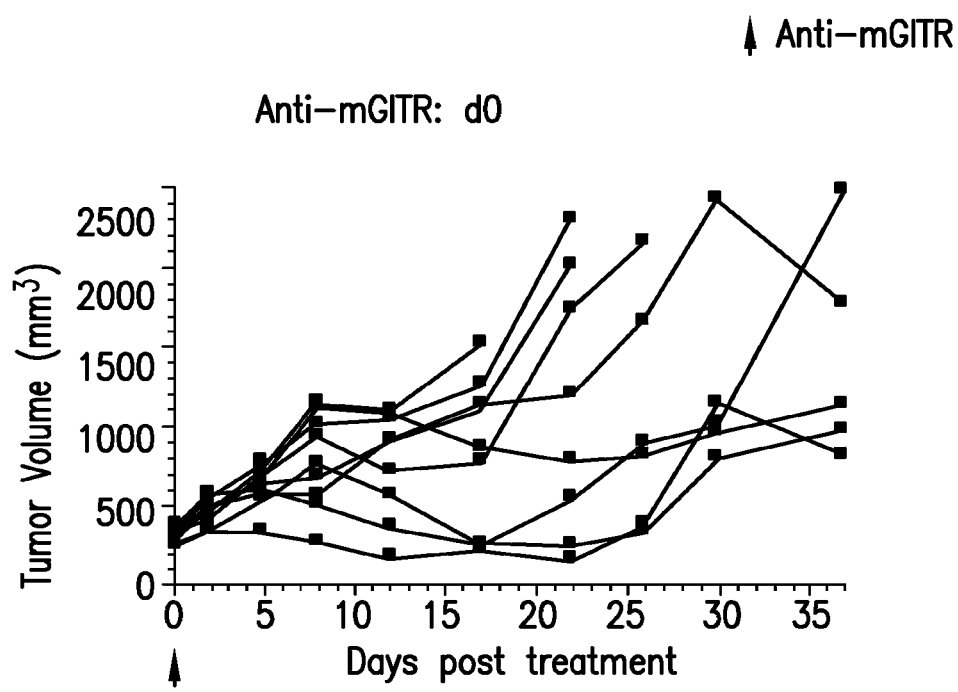
Figure 1G:
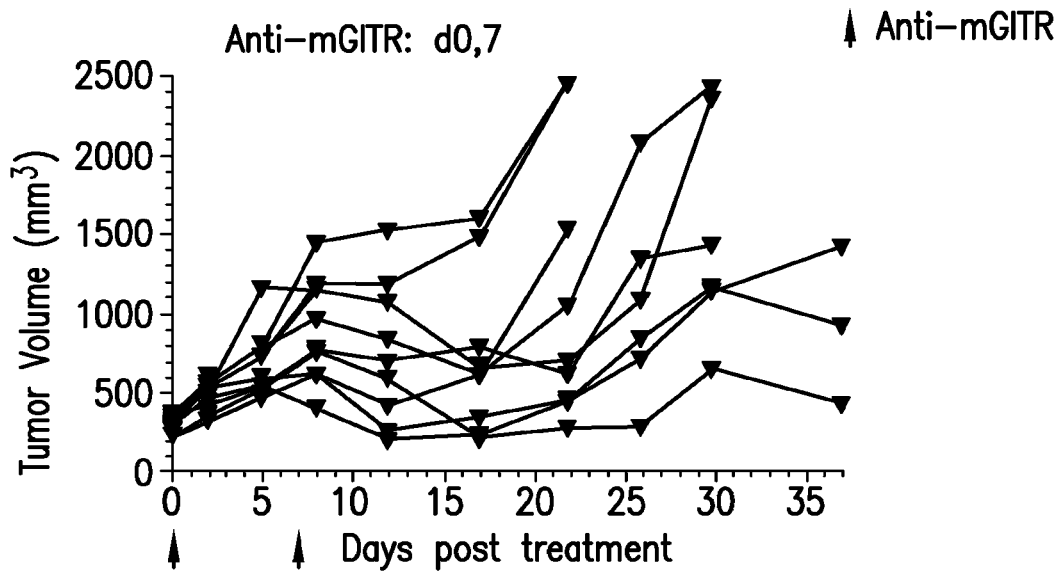
Figure 1H:
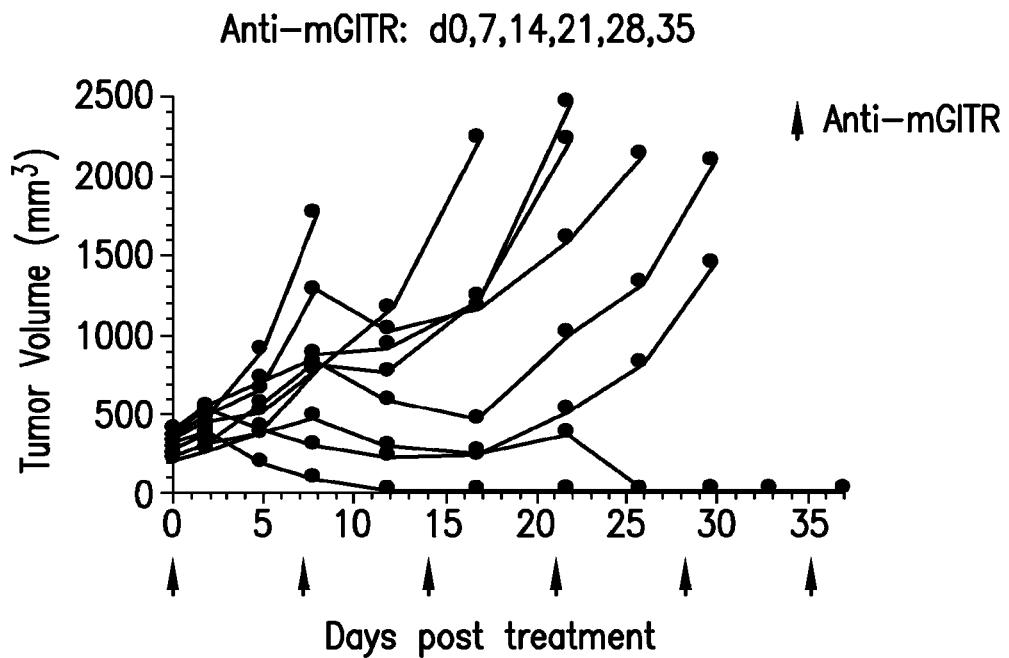
Figure 1I:
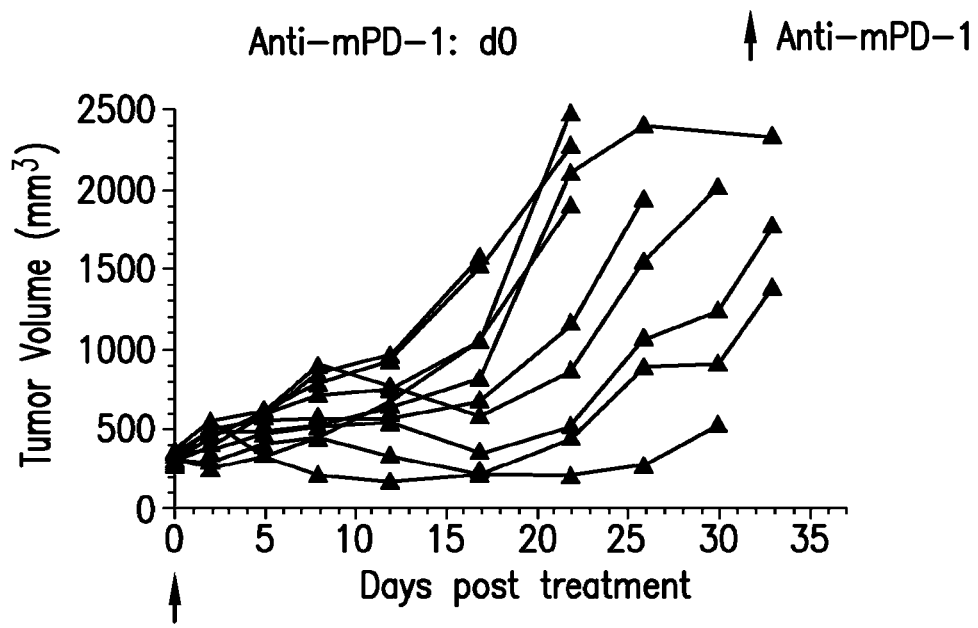
Figure 1J:
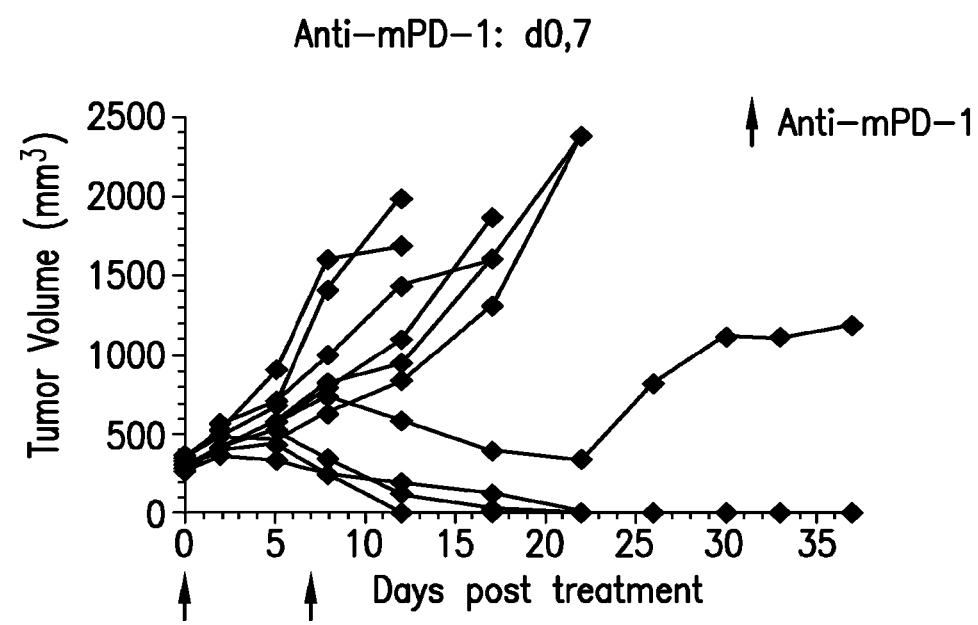
Figure 1K:
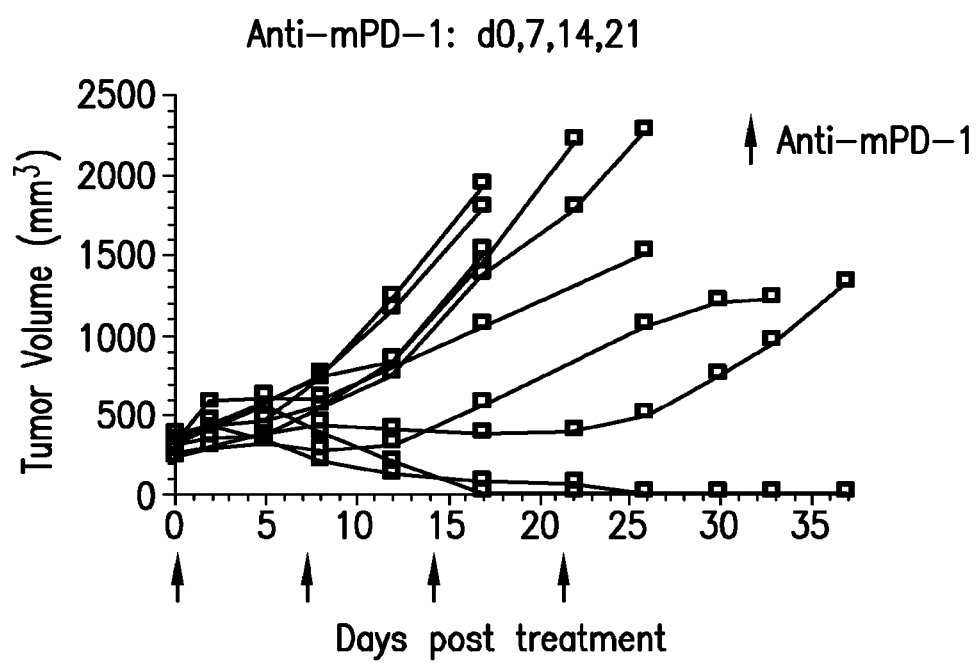
Figure 2A:
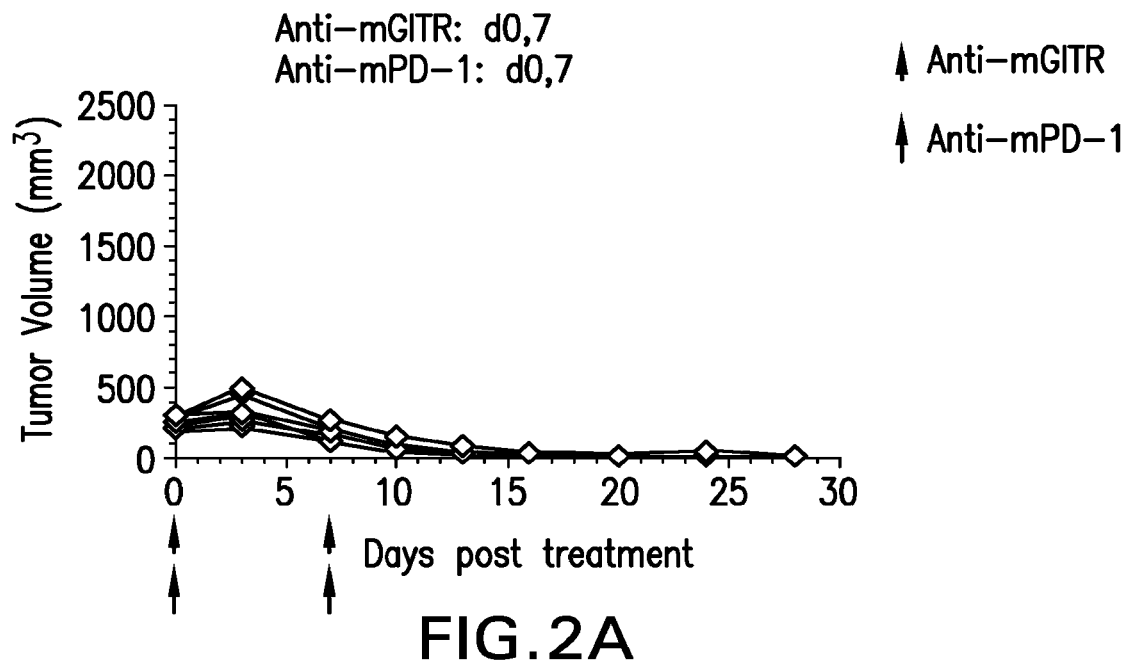
FIGS. 2A-2F show the anti-tumor efficacy of a single dose of anti-GITR antibodies followed by a single dose of anti-PD-1 antibodies one week later (FIG. 2B), or in the opposite sequence (FIG. 2C). This was compared to either antibody alone (FIGS. 2E-2F; n=10/group)
Figure 2B:
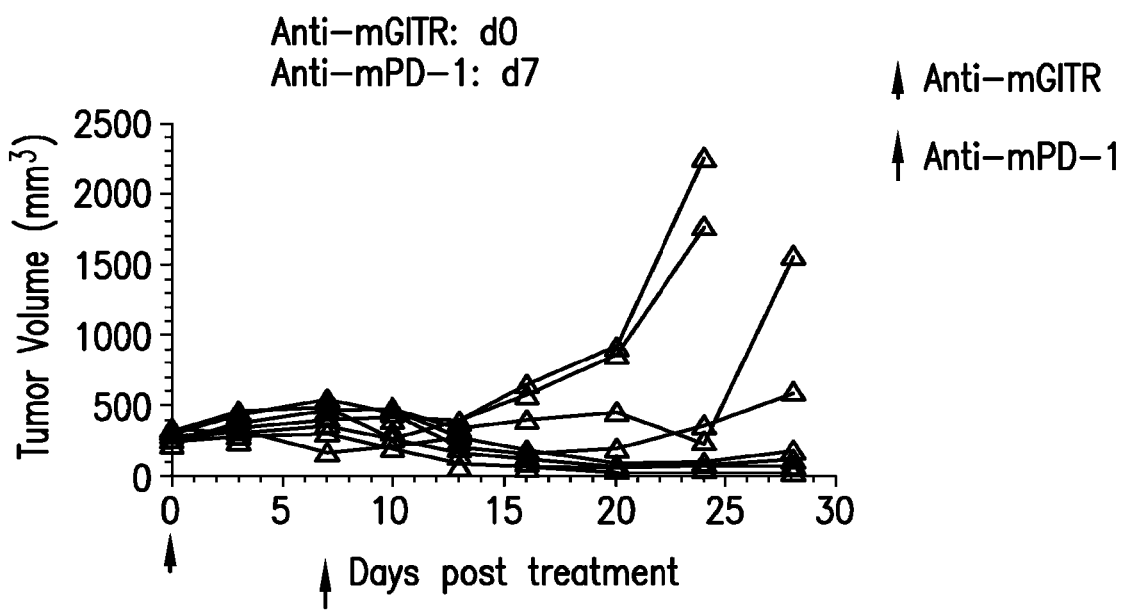
Figure 2C:
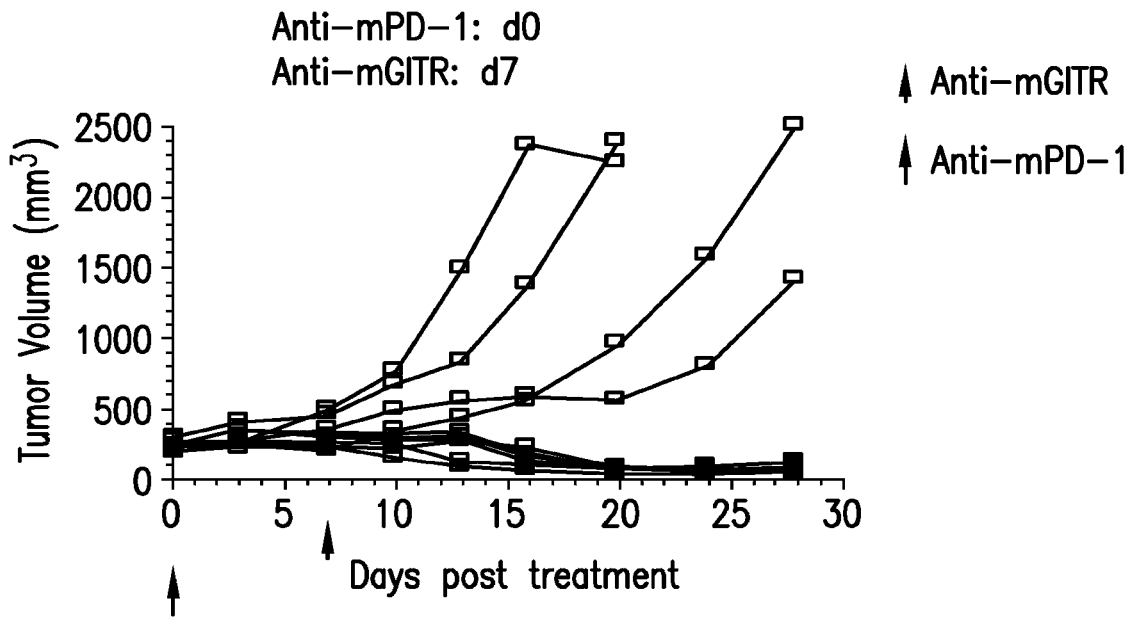
Figure 2D:
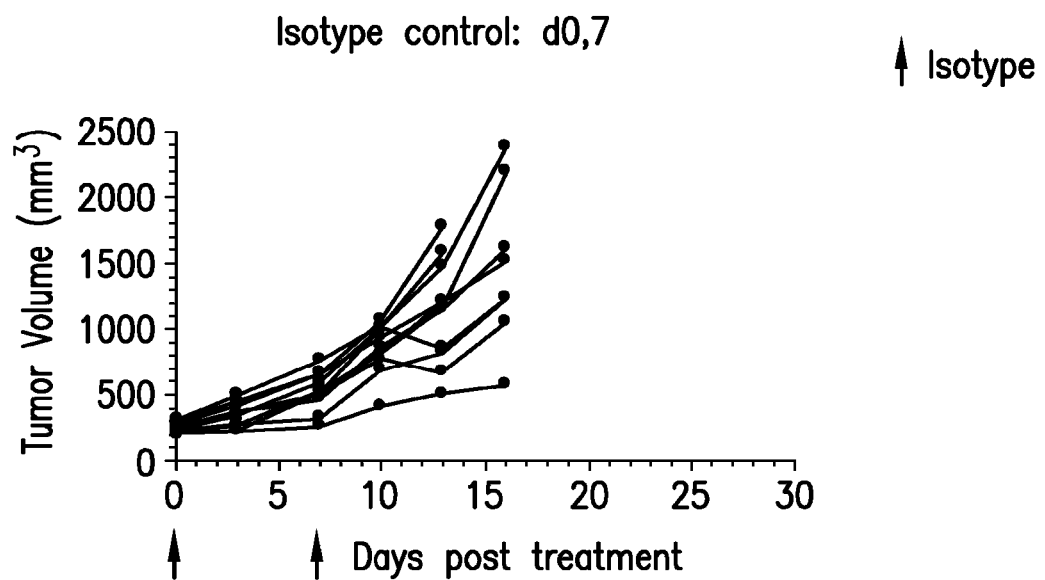
Figure 2E:
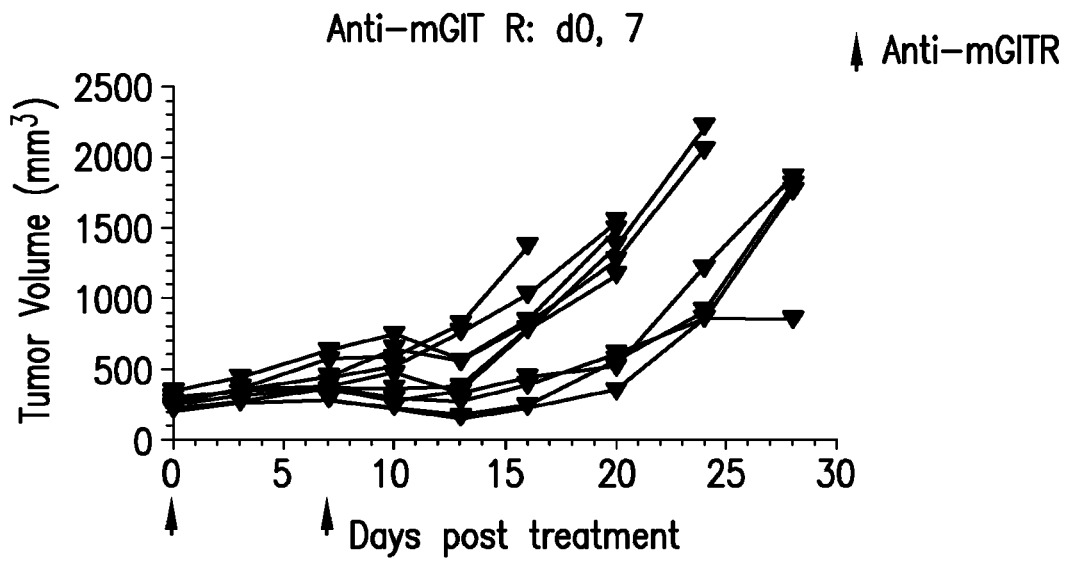
Figure 2F:
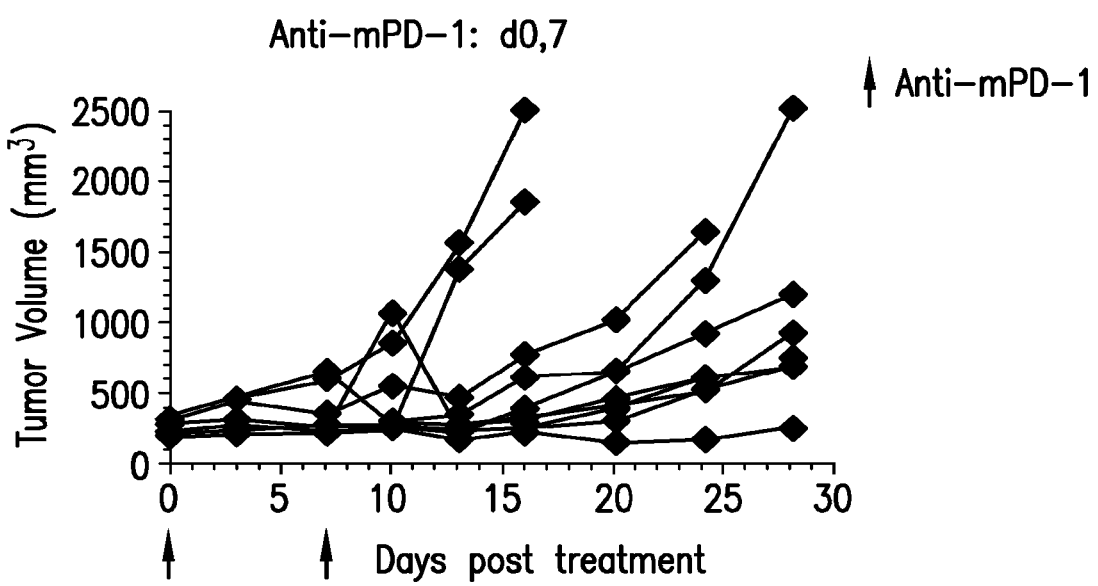
Figure 3A:
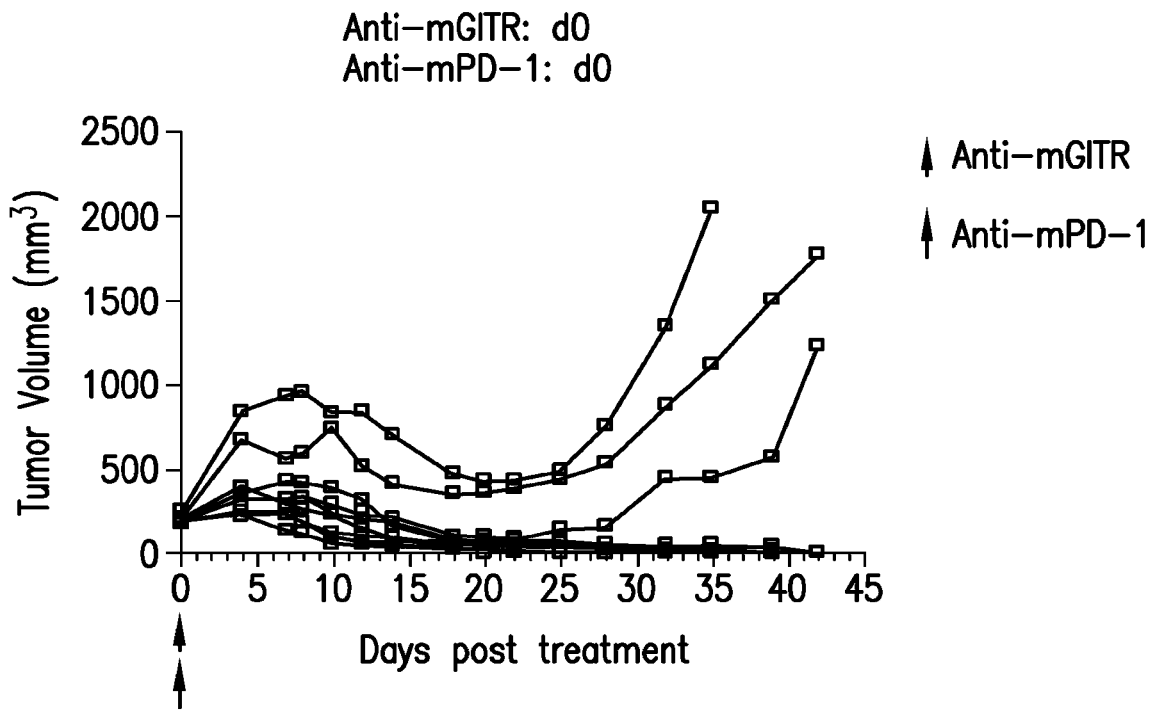
FIGS. 3A-3D show the anti-tumor efficacy of monotherapy of anti-GITR or anti-PD-1 antibodies alone (FIGS. 3C-3D), compared to co-administration of both antibodies (FIG. 3A) in the CT26 tumor model (n=10/group).
Figure 3B:
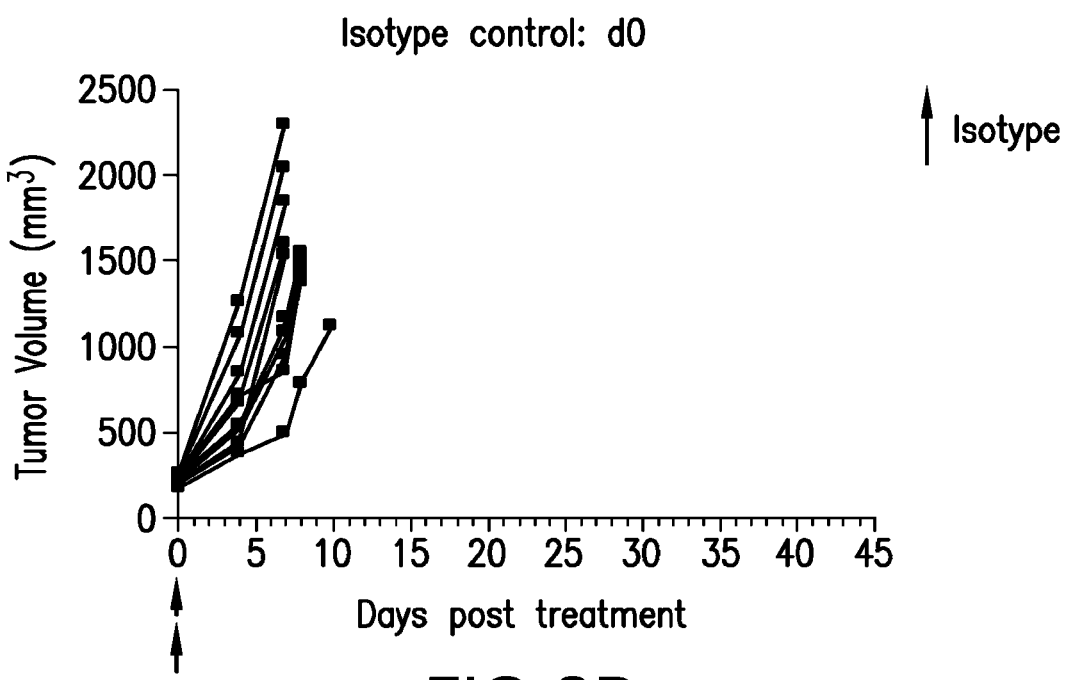
Figure 3C:
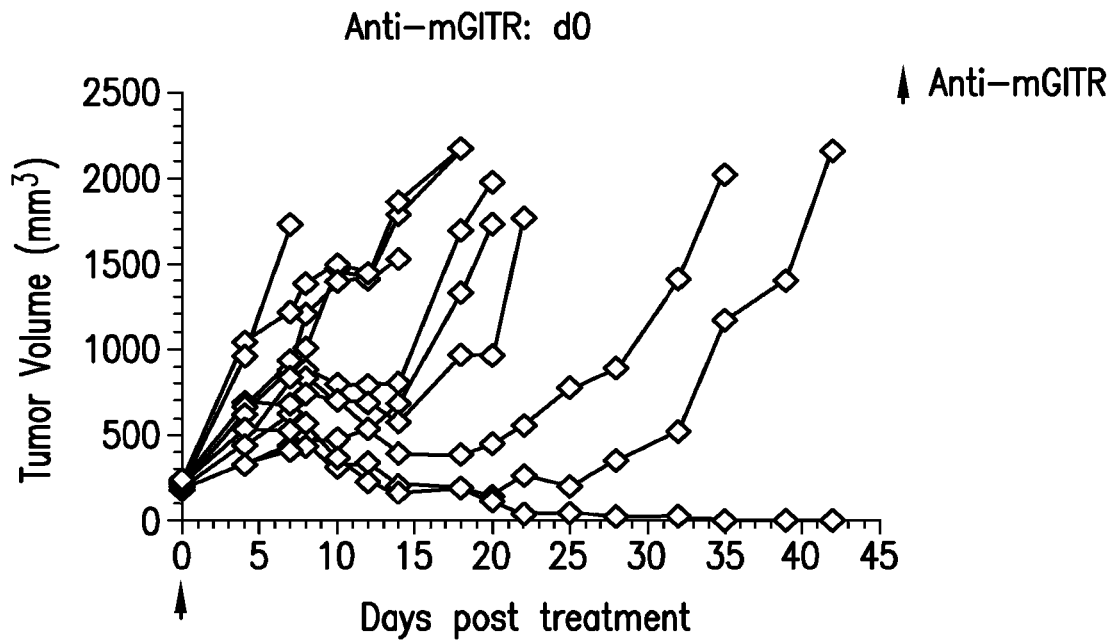
Figure 3D:
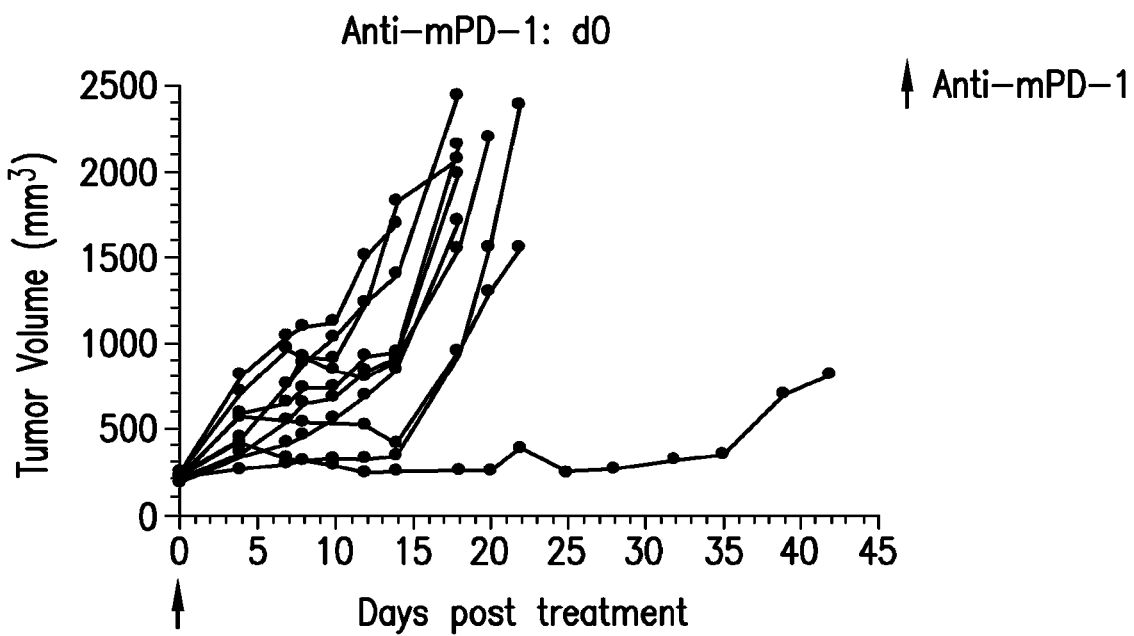
Figure 4A:
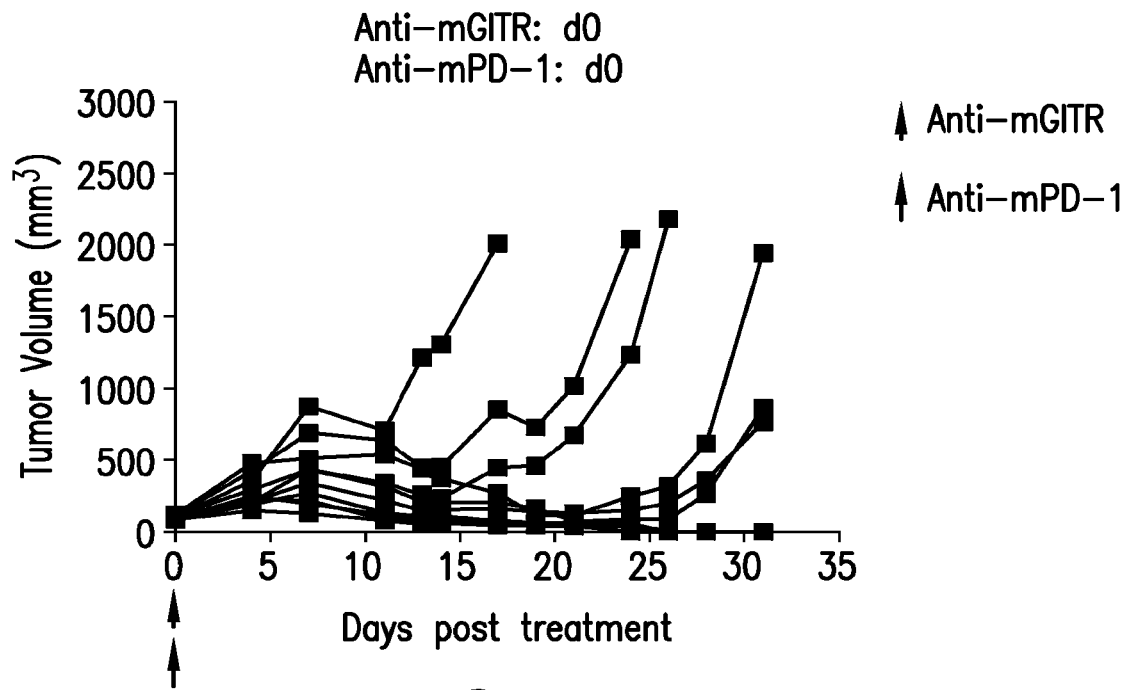
FIGS. 4A-4D show the effect of anti-GITR and anti PD-1 antibodies dosed alone or with concurrent administration of both antibodies on the anti-tumor response of mice implanted with the MB49 cell line (n=10/group). Treatment was commenced when tumors reached 85-122 mm$^3$.
Figure 4B:
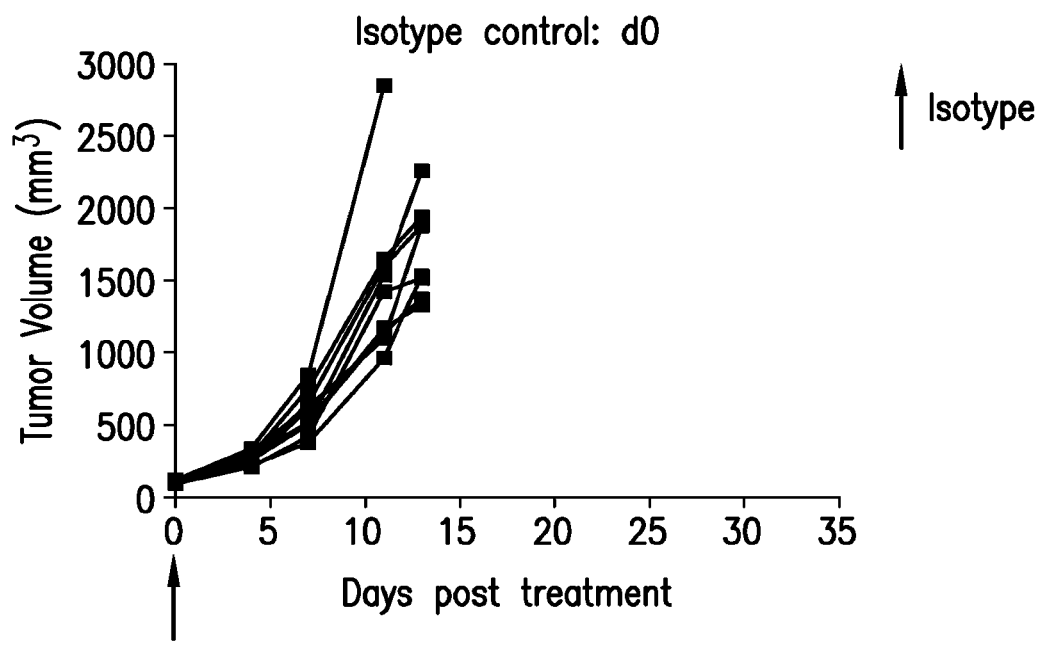
Figure 4C:
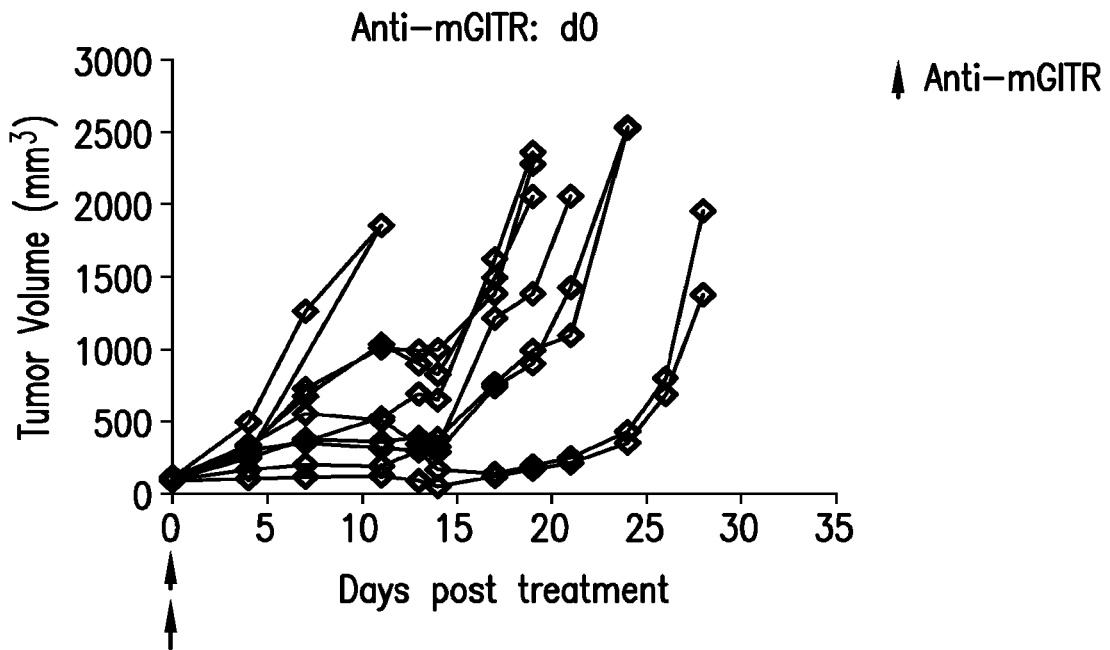
Figure 4D:
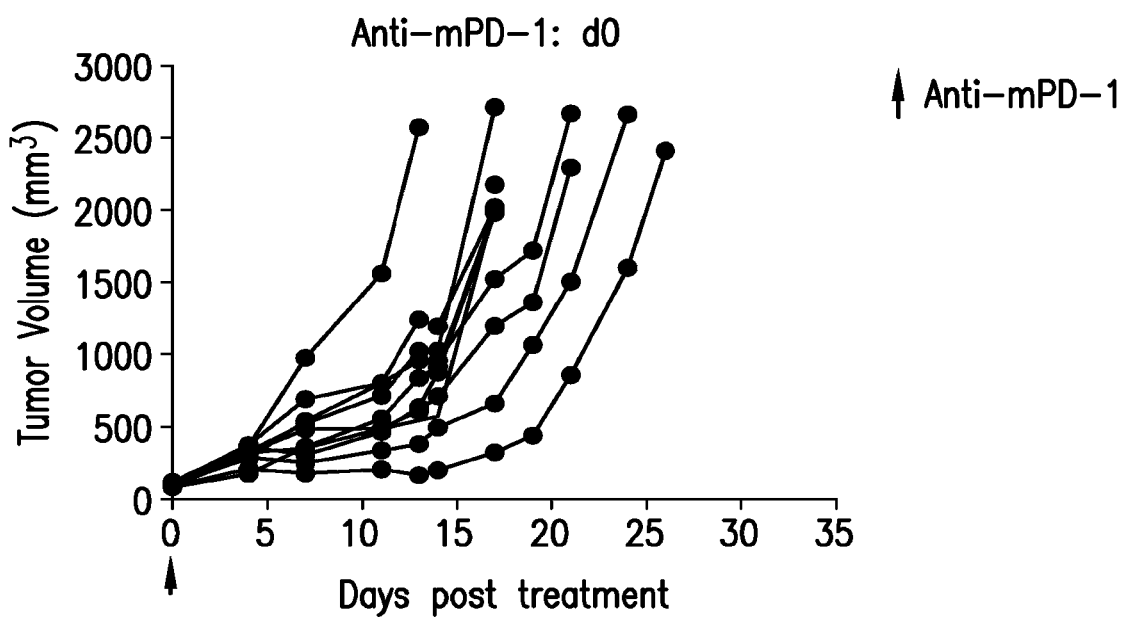

The present invention meets these needs in the art and more by providing a method of treating a tumor in a patient comprising administering to the patient a PD-1 antagonist and a GITR agonist, wherein the PD-1 antagonist and GITR agonist are administered simultaneously or sequentially. In certain embodiments, the PD-1 antagonist is an antibody or antigen binding fragment thereof, that binds PD-1 or PD-L1; and the GITR agonist is an antibody or antigen binding fragment thereof that binds GITR. The GITR agonist and PD-1 or PD-L1 antagonist binds to the human proteins. The antibody or binding fragment thereof is humanized or fully human.

In further embodiments, the PD-1 antagonist is selected from the group consisting of BMS-936558, MK-3475, and MPDL3280A; and GITR agonist is selected from the group consisting of an antibody having at least one CDR of SEQ ID NOs: 1-66; TRX518; and TRX385. The GITR agonist can be an antibody having: a heavy chain CDR1 of SEQ ID NOs: 1-11, CDR2 of SEQ ID NOs: 12-22, and CDR3 of SEQ ID NOs: 23-33; and/or a light chain CDR1 of SEQ ID NOs: 34-44, CDR2 of SEQ ID NOs: 45-55, and CDR3 of SEQ ID NOs: 56-66. In yet a further embodiment, the GITR agonist is an antibody having: a variable heavy chain of SEQ ID NOs: 67, 69, 71, 73, 75, 77, 79, 81, 83, 85, and 87; and/or a variable light chain of SEQ ID NO: 68, 70, 72, 74, 76, 78, 80, 82, 84, 86, and 88.

The present invention also contemplates that the PD-1 antagonist and GITR agonist are administered concurrently at least one time. In certain embodiments, the PD-1 antagonist and GITR agonist are administered concurrently at least 2 times. In certain embodiments, the tumor is an advanced stage tumor and can be selected from the group consisting of squamous cell cancer, small-cell lung cancer, non-small cell lung cancer, gastrointestinal cancer, pancreatic cancer, glioblastoma, glioma, cervical cancer, ovarian cancer, liver cancer such as hepatic carcinoma and hepatoma, bladder cancer, breast cancer, colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, and esophageal cancer.

The present invention provides method of treating a tumor, by administering to a patient a bispecific antibody comprising a first arm that binds to PD-1 or PD-L1 and antagonizes PD-1 activity, and a second arm that binds to GITR and agonizes GITR activity. In certain embodiments, the first arm is selected from the group consisting of an antigen binding fragment from BMS-936558, MK-3475, and MPDL3280A; and the second arm is selected from the group consisting of an antigen binding fragment from an antibody having at least one CDR of SEQ ID NO: 1-66; TRX518; and TRX385. In yet a further embodiment, the second arm has a heavy chain CDR1 of SEQ ID NOs: 1-11, CDR2 of SEQ ID NOs: 12-22, and CDR3 of SEQ ID NOs: 23-33; and/or a light chain CDR1 of SEQ ID NOs: 34-44, CDR2 of SEQ ID NOs: 45-55, and CDR3 of SEQ ID NOs: 56-66. In certain embodiments, the second arm has a variable heavy chain of SEQ ID NOs: 67, 69, 71, 73, 75, 77, 79, 81, 83, 85, and 87; and/or a variable light chain of SEQ ID NO: 68, 70, 72, 74, 76, 78, 80, 82, 84, 86, and 88.

The present invention provides a method of treating a tumor wherein the tumor is an advanced stage tumor. In certain embodiments, the advanced stage tumor is selected from the group consisting of squamous cell cancer, small-cell lung cancer, non-small cell lung cancer, gastrointestinal cancer, pancreatic cancer, glioblastoma, glioma, cervical cancer, ovarian cancer, liver cancer such as hepatic carcinoma and hepatoma, bladder cancer, breast cancer, colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, and esophageal cancer.

The present invention provides a pharmaceutical composition comprising a PD-1 antagonist and a GITR agonist. Also provided is the use of a PD-1 antagonist in combination with a GITR agonist to treat an advanced stage tumor.

DETAILED DESCRIPTION

As used herein, including the appended claims, the singular forms of words such as "a," "an," and "the," include their corresponding plural references unless the context clearly dictates otherwise. Table 15 below provides a listing of sequence identifiers used in this application. All references cited herein are incorporated by reference to the same extent as if each individual publication, database entry (e.g. GenBank sequences or GeneID entries), patent application, or patent, was specifically and individually indicated to be incorporated by reference. Citation of the references herein is not intended as an admission that any of the foregoing is pertinent prior art, nor does it constitute any admission as to the contents or date of these publications or documents.

I. Definitions

The term "glucocorticoid-induced TNF receptor" (abbreviated herein as "GITR"), also known as TNF receptor superfamily 18 (TNFRSF18), TEASR, and 312C2, as used herein, refers to a member of the tumor necrosis factor/nerve growth factor receptor family. GITR is a 241 amino acid type I transmembrane protein characterized by three cysteine pseudo-repeats in the extracellular domain and specifically protects T-cell receptor-induced apoptosis, although it does not protect cells from other apoptotic signals, including Fas triggering, dexamethasone treatment, or UV irradiation (Nocentini, G., et al. (1997) *Proc. Natl. Acad. Sci. USA* 94:6216-622). The nucleic acid and amino acid sequences of human GITR (hGITR), of which there are three splice variants, are known and can be found in, for example GenBank Accession Nos. gi:40354198, gi:23238190, gi:23238193, and gi:23238196.

"GITR agonist" means any chemical compound or biological molecule that stimulates an immune reaction through activation of GITR signaling. Sequences of agonist anti-GITR antibodies are provided in WO 2011/028683 and WO 2006/105021, as well as TRX-385 and TRX-518. Also contemplated are soluble GITR-L proteins, a GITR binding partner.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: Programmed death receptor 1; PDCD1, PD1, CD279 and SLEB2 for PD-1; PDCD1L1, PDL1, B7H1, B7-4, CD274 and B7-H for PD-L1; and Programmed death receptor Ligand 1, PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and are useful in the treatment method, medicaments and uses of the present invention, are described in U.S. Pat. Nos. 7,521,051, 8,008,449, and 8,354,509. Specific anti-human PD-1 mAbs useful as the PD-1 antagonist in the treatment method, medicaments and uses of the present invention include: MK-3475, a humanized IgG4 mAb with the structure described in WHO Drug Information, Vol. 27, No. 2, pages 161-162 (2013) and which comprises the heavy and light chain amino acid sequences shown in FIG. 6, nivolumab (BMS-936558), a human IgG4 mAb with the structure described in WHO Drug Information, Vol. 27, No. 1, pages 68-69 (2013) and which comprises the heavy and light chain amino acid sequences shown in FIG. 7; pidilizumab (CT-011, also known as hBAT or hBAT-1); and the humanized antibodies h409A11, h409A16 and h409A17, which are described in WO2008/156712.

Examples of mAbs that bind to human PD-L1, and are useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

The term "administering" as used herein refers to the physical introduction of a composition comprising a GITR agonist and at least one additional cancer therapeutic agent, e.g., a PD-1 antagonist to a patient with cancer. Any and all methods of introduction are contemplated according to the invention; the method is not dependent on any particular means of introduction. Means of introduction are well-known to those skilled in the art, examples of which are provided herein.

The term "co-administering" as used herein means a process whereby the combination of a GITR agonist and at least one additional cancer therapeutic agent, e.g., a PD-1 antagonist, is administered to the same patient. The GITR agonist and PD-1 antagonist may be administered concurrently or sequentially. If administration takes place sequentially, the GITR agonist and/or PD-1 antagonist may be administered before or after a given additional cancer therapeutic agent or treatment. The GITR agonist and PD-1 antagonist treatment need not be administered by means of the same vehicle. The GITR agonist and PD-1 antagonist may be administered one or more times and the number of administrations of each component of the combination may be the same or different. In addition, GITR agonist and PD-1 antagonist need not be administered at the same site.

The term "therapeutically effective amount" or "therapeutically effective combination" as used herein refers to an amount or dose of a GITR agonist, together with the amount or dose of an additional agent or treatment, e.g., a PD-1 antagonist that is sufficient to modulate, e.g., stimulate, the systemic immune response of an individual. The amount of each molecule in a given therapeutically effective combination may be different for different individuals and different tumor types, and will be dependent upon the one or more additional agents or treatments included in the combination. The "therapeutically effective amount" is determined using procedures routinely employed by those of skill in the art such that an "improved therapeutic outcome" results.

As used herein, the terms "improved therapeutic outcome" and "enhanced therapeutic efficacy," relative to cancer refers to a slowing or diminution of the growth of cancer cells or a solid tumor, or a reduction in the total number of cancer cells or total tumor burden. An "improved therapeutic outcome" or "enhanced therapeutic efficacy" therefore means there is an improvement in the condition of the patient according to any clinically acceptable criteria, including, for example, decreased tumor size, an increase in time to tumor progression, increased progression-free survival, increased overall survival time, an increase in life expectancy, or an improvement in quality of life. In particular, "improved" or "enhanced" refers to an improvement or enhancement of 1%, 5%, 10%, 25% 50%, 75%, 100%, or greater than 100% of any clinically acceptable indicator of therapeutic outcome or efficacy.

As used herein, the term "antibody" refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

As used herein, the terms "GITR, PD-1, or PD-L1 binding fragment," "binding fragment thereof" or "antigen binding fragment thereof" encompass a fragment or a derivative of an antibody that still substantially retains its biological activity of inducing GITR signaling referred to herein as "GITR inducing activity." Alternatively, PD-1 or PD-L1 binding fragment encompasses a fragment or derivative of antibody that inhibits PD-1 activity, e.g., binding to PD-L1 or PD-L2. The term "antibody fragment" or GITR, PD-1, or PD-L1 binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its GITR agonist activity. Preferably, a binding fragment or derivative retains at least 25%, 50%, 60%, 70%, 80%, 90%, 95%, 99% or 100% (or more) of its GITR agonist or PD-1 antagonist activity, although any binding fragment with sufficient affinity to exert the desired biological effect will be useful. It is also intended that a GITR, PD-1, or PD-L1 binding fragment can include variants having conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson, et al. (1991) *Nature* 352: 624-628 and Marks, et al. (1991)*J. Mol. Biol.* 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison, et al. (1984) *Proc. Natl. Acad. Sci. USA* 81: 6851-6855.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. A "domain antibody fragment" is an immunologically functional immunoglobulin fragment containing only the variable region of a heavy chain or the variable region of a light chain. In some instances, two or more $V_H$ regions are covalently joined with a peptide linker to create a multivalent domain antibody fragment. The two $V_H$ regions of a bivalent domain antibody fragment may target the same or different antigens. See, e.g., Muyldermans, et al. (2001) *Trends Biochem. Sci.* 26:230; Reichmann, et al. (1999) *J. Immunol. Methods* 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger, et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively. A fully human antibody may be generated in a human being, in a transgenic animal having human immunoglobulin germline sequences, by phage display or other molecular biological methods. Exemplary techniques that can be used to make antibodies are described in U.S. Pat. Nos. 6,150,584; 6,458,592; 6,420,140. Other techniques, such as the use of libraries, are known in the art.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The antibodies of the present invention also include antibodies with intact Fc regions that provide full effector functions, e.g. antibodies of isotype IgG1, which induce complement-dependent cytotoxicity (CDC) or antibody dependent cellular cytotoxicity (ADCC) in a targeted cell.

The antibodies of the present invention also include antibodies conjugated to cytotoxic payloads, such as cytotoxic agents or radionuclides. Such antibody conjugates may be used in immunotherapy in conjunction with anti-GITR, anti-PD-1, or anti PD-L1 treatment, to selectively target and kill cells expressing certain antigens on their surface. Exemplary cytotoxic agents include ricin, vinca alkaloid, methotrexate, *Psuedomonas* exotoxin, saporin, diphtheria toxin, cisplatin, doxorubicin, abrin toxin, gelonin and pokeweed antiviral protein. Exemplary radionuclides for use in immunotherapy with the antibodies of the present invention include $^{125}$I, $^{131}$I, $^{90}$Y, $^{67}$Cu, $^{211}$At, $^{177}$Lu, $^{143}$Pr and $^{213}$Bi. See, e.g., U.S. Patent Application Publication No. 2006/0014225.

Bispecific antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein, et al. (1983) *Nature* 305: 537-39. Alternatively, bispecific antibodies can be prepared using chemical linkage. See, e.g., Brennan, et al. (1985) *Science* 229:81. Bispecific antibodies include bispecific antibody fragments. See, e.g., Holliger, et al. (1993) *Proc. Natl. Acad. Sci. U.S.A.* 90:6444-48, Gruber, et al. (1994) *J. Immunol.* 152:5368.

The term "multispecific" includes binding molecules having specificity for more than one target antigen. Such molecules have more than one binding site where each binding site specifically binds (e.g., immunoreacts with) a different target molecule or a different antigenic site on the same target. In one embodiment, a multispecific binding molecule of the invention is a bispecific molecule (e.g., antibody, minibody, domain deleted antibody, or fusion protein) having binding specificity for at least two targets, e.g., more than one target molecule or more than one epitope on the same target molecule.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system.

"Binding compound" refers to a molecule, small molecule, macromolecule, polypeptide, antibody or fragment or analogue thereof, or soluble receptor, capable of binding to a target. "Binding compound" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, that is capable of binding to a target. When used with reference to antibodies, the term "binding compound" refers to both antibodies and antigen binding fragments thereof "Binding" refers to an association of the binding composition with a target where the association results in reduction in the normal Brownian motion of the binding composition, in cases where the binding composition can be dissolved or suspended in solution. "Binding composition" refers to a molecule, e.g. a binding compound, in combination with a stabilizer, excipient, salt, buffer, solvent, or additive, capable of binding to a target.

As used herein, "conservatively modified variants" of or "conservative substitution" refers to substitutions of amino acids that are known to those of skill in this art and may often be made even in essential regions of the antibody without altering the biological activity of the resulting antibody. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Those of skill in this art recognize that, in general, single amino acid substitutions in non-essential regions of a polypeptide may not substantially alter biological activity. See, e.g., Watson, et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Proliferative activity" encompasses an activity that promotes, that is necessary for, or that is specifically associated with, e.g., normal cell division, as well as cancer, tumors, dysplasia, cell transformation, metastasis, and angiogenesis.

The terms "cancer", "tumor", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer, colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer.

As cancerous cells grow and multiply, they form a mass of cancerous tissue, that is a tumor, which invades and destroys normal adjacent tissues. Malignant tumors are cancer. Malignant tumors usually can be removed, but they may grow back. Cells from malignant tumors can invade and damage nearby tissues and organs. Also, cancer cells can break away from a malignant tumor and enter the bloodstream or lymphatic system, which is the way cancer cells spread from the primary tumor (i.e., the original cancer) to form new tumors in other organs. The spread of cancer in the body is called metastasis (What You Need to Know About Cancer—an Overview, NIH Publication No. 00-1566; posted Sep. 26, 2000, updated Sep. 16, 2002 (2002)).

As used herein, the term "solid tumor" refers to an abnormal growth or mass of tissue that usually does not contain cysts or liquid areas. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone barrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MM) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

As used herein, the term "primary cancer" refers to the original tumor or the first tumor. Cancer may begin in any organ or tissue of the body. It is usually named for the part of the body or the type of cell in which it originates (Metastatic Cancer: Questions and Answers, Cancer Facts 6.20, National Cancer Institute, reviewed Sep. 1, 2004 (2004)).

As used herein, the term "carcinoma in situ" refers to cancerous cells that are still contained within the tissue where they started to grow, and have not yet become invasive or spread to other parts of the body.

As used herein, the term "carcinomas" refers to cancers of epithelial cells, which are cells that cover the surface of the body, produce hormones, and make up glands. Examples of carcinomas are cancers of the skin, lung, colon, stomach, breast, prostate and thyroid gland.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences involved in the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis, et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences, including rodent (e.g. mouse) and human germline sequences. Any suitable source of unrearranged immunoglobulin DNA may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

To examine the extent of enhancement of, e.g., GITR activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) Glia 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Small molecule" is defined as a molecule with a molecular weight that is less than 10 kDa, typically less than 2 kDa, and preferably less than 1 kDa. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described. See, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482.

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence (in this case GITR) if it binds to polypeptides comprising the sequence of GITR but does not bind to proteins lacking the sequence of GITR. For example, an antibody that specifically binds to a polypeptide comprising GITR may bind to a FLAG®-tagged form of GITR but will not bind to other FLAG®-tagged proteins.

The term "epitope" or "antigenic determinant" refers to a site on an antigen to which a binding molecule specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, X-ray crystallography and 2-dimensional nuclear magnetic resonance.

Binding molecules that recognize the same epitope can be identified in a simple immunoassay showing the ability of one antibody to block the binding of another antibody to a target antigen, i.e., a competitive binding assay. Competitive binding is determined in an assay in which the binding molecule being tested inhibits specific binding of a reference binding molecule to a common antigen, such as GITR. Numerous types of competitive binding assays are known, for example: solid phase direct or indirect radioimmunoassay (RIA); solid phase direct or indirect enzyme immunoassay (EIA) sandwich competition assay (see Stahli, et al., (1983) *Methods in Enzymology* 9:242); solid phase direct biotin-avidin EIA (see Kirkland, et al., (1986) *J. Immunol.* 137:3614); solid phase direct labeled assay, solid phase direct labeled sandwich assay (see Harlow and Lane, (1988) *Antibodies: A Laboratory Manual*, Cold Spring Harbor Press); solid phase direct label RIA using 1-125 label (see Morel, et al., (1988) *Mol. Immunol.* 25(1):7); solid phase direct biotin-avidin EIA (Cheung, et al., (1990) *Virology* 176:546); and direct labeled RIA. (Moldenhauer, et al., (1990) *Scand. J. Immunol.* 32:77).

Typically, such an assay involves the use of purified antigen bound to a solid surface or cells bearing either of these, an unlabeled test binding molecule and a labeled reference binding molecule. Competitive inhibition is measured by determining the amount of label bound to the solid surface or cells in the presence of the test binding molecule. Usually the test binding molecule is present in excess. Usually, when a competing binding molecule is present in excess, it will inhibit specific binding of a reference binding molecule to a common antigen by at least 50-55%, 55-60%, 60-65%, 65-70% 70-75% or more.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen, et al. (1980) *Analyt. Biochem.* 107:220-239.

II. General

The present invention provides methods of treating advanced stage tumors with a combination of GITR agonists and PD-1 antagonists, including anti-GITR and anti-PD-1 or anti-PD-L1 antibodies.

III. Pharmaceutical Compositions

To prepare pharmaceutical or sterile compositions, the GITR, PD-1, or PD-L1 antibodies are admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions. See, e.g., Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio of $LD_{50}$ to $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

The mode of administration is not particularly important. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is substantially derived from the same species as the animal targeted for treatment (e.g. a humanized antibody for treatment of human subjects), thereby minimizing any immune response to the reagent.

Antibodies and antibody fragments can be provided by continuous infusion, or by doses at intervals of, e.g., one day, 1-7 times per week, one week, two weeks, monthly, bimonthly, etc. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

Methods for co-administration or treatment with a second therapeutic agent, e.g., a cytokine, antibody, steroid, chemotherapeutic agent, antibiotic, anti-viral, or radiation, are well known in the art, see, e.g., Hardman, et al. (eds.) (2001) *Goodman and Gilman's The Pharmacological Basis of Therapeutics*, 10th ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa. In particular, administration of PD-1 or PD-L1 antibodies can occur simultaneously or sequentially. In particular embodiments, the anti-GITR antibody can be administered first followed by periodic (e.g. one week later or weekly) dosing of an anti-PD-1, or anti-PD-L1 antibodies. Alternatively, treatment with anti-PD-1 or PD-L1 antibodies can be followed by treatment with anti-GITR antibodies on a similar schedule. In further embodiments, anti-GITR antibodies are co-administered with anti-PD-1 or anti-PD-L1 in at least a single treatment or multiple doses (e.g., weekly administration).

The GITR, PD-1 or PD-L1 antibodies can be combined with chemotherapeutic agents including alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. *Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; XELODA® capecitabine; ibandronate; CPT-11; topoisomerase inhibitor RFS 2000; difluoromethylornithine (DMFO); retinoids such as retinoic acid; and pharmaceutically acceptable salts, acids or derivatives of any of the above.

Also included are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON. toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A combination therapy is used to treat an advanced stage tumor having dimensions of at least about 175 mm$^3$. In another embodiment of the invention, a combination therapy is used to treat a tumor that is at least about 200 mm$^3$, 300 mm$^3$, 400 mm$^3$, 500 mm$^3$, 750 mm$^3$, up to 1000 mm$^3$. A combination therapy of the invention is used to treat a tumor that is large enough to be found by palpation or by imaging techniques well known in the art, such as MRI, ultrasound, or CAT scan.

A "synergistic effect" of two compounds is one in which the effect of the combination of the two agents is greater than the sum of their individual effects and is statistically different from the controls and the single drugs. In another embodiment, the combination therapies of the invention have an additive effect. An "additive effect" of two compounds is one in which the effect of the combination of the two agents is the sum of their individual effects and is statistically different from either the controls and/or the single drugs.

The subject methods result in an inhibition of tumor size more than about 10%, more than about 20%, more than about 30%, more than about 35%, more than about 42%, more than about 43%, more than about 44%, more than about 45%, more than about 46%, more than about 47%, more than about 48%, more than about 49%, more than about 50%, more than about 51%, more than about 52%, more than about 53%, more than about 54%, more than about 55%, more than about 56%, more than about 57%, more than about 58%, more than about 59%, more than about 60%, more than about 65%, more than about 70%, more than about 75%, more than about 80%, more than about 85%, more than about 90%, more than about 95%, or more than about 100%. In one embodiment, the administration of a GITR binding molecule in conjunction with a PD-1 antagonist molecule can lead to complete regression of an advanced tumor.

Also contemplated is co-administration of the GITR agonist/PD-1 antagonist combination with anti-viral therapeutics. Anti-virals include any drug that destroys viruses. Antivirals may include interferons, which function to inhibit replication of the virus, protease inhibitors, and reverse transcriptase inhibitors or agents contained in the combination of highly active antiretroviral therapy (HAART) for HIV.

Typical veterinary, experimental, or research subjects include monkeys, dogs, cats, rats, mice, rabbits, guinea pigs, horses, and humans.

IV. Uses

Cancer

The GITR, PD-1, or PD-L1 antibodies or antigen binding fragments can be used to treat cancer (i.e., to inhibit the growth or survival of tumor cells). Preferred cancers whose growth may be inhibited using the antibodies of the invention include cancers typically responsive to immunotherapy, but also cancers that have not hitherto been associated with immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Additionally, the invention includes refractory or recurrent malignancies whose growth may be inhibited using the antibodies of the invention.

The GITR agonist/PD-1 antagonist antibody or antigen binding fragments can be used alone or in combination with: other anti-neoplastic agents or immunogenic agents (for example, attenuated cancerous cells, tumor antigens (including recombinant proteins, peptides, and carbohydrate molecules), antigen presenting cells such as dendritic cells pulsed with tumor derived antigen or nucleic acids, immune stimulating cytokines (for example, IL-2, IFNa2, GM-CSF), and cells transfected with genes encoding immune stimulating cytokines such as but not limited to GM-CSF); standard cancer treatments (for example, chemotherapy, radiotherapy or surgery); or other antibodies (including but not limited to antibodies to VEGF, EGFR, Her2/neu, VEGF receptors, other growth factor receptors, CD20, CD40, CTLA-4, OX-40, 4-IBB, and ICOS).

Infectious Diseases

The GITR agonist/PD-1 antagonist combination can also be used to prevent or treat infections and infectious disease. The GITR agonist/PD-1 antagonist combination can be used alone, or in conjunction with vaccines, to stimulate the immune response to pathogens, toxins, and self-antigens. The antibodies or antigen-binding fragment thereof can be used to stimulate immune response to viruses infectious to humans, such as, but not limited to, human immunodeficiency viruses, hepatitis viruses class A, B and C, Eppstein Barr virus, human cytomegalovirus, human papilloma viruses, herpes viruses. The antibodies or antigen-binding fragment thereof can be used to stimulate immune response to infection with bacterial or fungal parasites, and other pathogens.

Vaccination Adjuvants

The GITR agonist/PD-1 antagonist antibody or antibody fragment combination can be used in conjunction with other recombinant proteins and/or peptides (such as tumor antigens or cancer cells) in order to increase an immune response to these proteins (i.e., in a vaccination protocol).

For example, GITR agonist/PD-1 antagonist antibodies and antibody fragments thereof may be used to stimulate antigen-specific immune responses by co-administration of the GITR agonist/PD-1 antagonist combination with an antigen of interest (e.g., a vaccine). Accordingly, in another aspect the invention provides a method of enhancing an immune response to an antigen in a subject, comprising administering to the subject: (i) the antigen; and (ii) a GITR agonist/PD-1 antagonist combination, such that an immune response to the antigen in the subject is enhanced. The antigen can be, for example, a tumor antigen, a viral antigen, a bacterial antigen or an antigen from a pathogen.

Ex-Vivo Activation of T Cells

The antibodies and antigen fragments of the invention can also be used for the ex vivo activation and expansion of antigen specific T cells and adoptive transfer of these cells into recipients in order to increase antigen-specific T cells against tumor. These methods may also be used to activate T cell responses to infectious agents such as CMV. Ex vivo activation in the presence of the GITR agonist/PD-1 antagonist combination may be expected to increase the frequency and activity of the adoptively transferred T cells.

EXAMPLES

Example 1

General Methods

Standard methods in molecular biology are described. Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif. Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described. Coligan, et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra. Standard techniques for characterizing ligand/receptor interactions are available. See, e.g., Coligan, et al. (2001) *Current Protcols in Immunology*, Vol. 4, John Wiley, Inc., New York.

Monoclonal, polyclonal, and humanized antibodies can be prepared (see, e.g., Sheperd and Dean (eds.) (2000) Monoclonal Antibodies, Oxford Univ. Press, New York, N.Y.; Kontermann and Dubel (eds.) (2001) Antibody Engineering, Springer-Verlag, New York; Harlow and Lane (1988) Antibodies A Laboratory Manual, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang, et al. (1999) *J. Biol. Chem.* 274:27371-27378; Baca, et al. (1997) *J. Biol. Chem.* 272:10678-10684; Chothia, et al. (1989) *Nature* 342:877-883; Foote and Winter (1992)*J. Mol. Biol.* 224:487-499; U.S. Pat. No. 6,329,511).

An alternative to humanization is to use human antibody libraries displayed on phage or human antibody libraries in transgenic mice (Vaughan, et al. (1996) *Nature Biotechnol.* 14:309-314; Barbas (1995) *Nature Medicine* 1:837-839; Mendez, et al. (1997) *Nature Genetics* 15:146-156; Hoogenboom and Chames (2000) *Immunol. Today* 21:371-377; Barbas, et al. (2001) Phage Display: A Laboratory Manual, Cold Spring Harbor Laboratory Press, Cold Spring Harbor, N.Y.; Kay, et al. (1996) Phage Display of Peptides and Proteins: A Laboratory Manual, Academic Press, San Diego, Calif.; de Bruin, et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard, et al. (1997) *Immunity* 7:283-290; Wright, et al. (2000) *Immunity* 13:233-242; Preston, et al., supra; Kaithamana, et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal, et al. (1991) *J. Immunol.* 146:169-175; Gibellini, et al. (1998) *J. Immunol.* 160:3891-3898; Hsing and Bishop (1999) *J. Immunol.* 162:2804-2811; Everts, et al. (2002) *J. Immunol.* 168:883-889).

Methods for flow cytometry, including fluorescence activated cell sorting detection systems (FACS®), are available. See, e.g., Owens et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) Catalogue, Molecular Probes, Inc., Eugene, Oreg.; Sigma-Aldrich (2003) Catalogue, St. Louis, Mo.

Standard methods of histology of the immune system are described. See, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.

Software packages and databases for determining, e.g., antigenic fragments, leader sequences, protein folding, functional domains, glycosylation sites, and sequence alignments, are available. See, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690.

Example 2

In Vivo Treatment Methods

Approximately eight to ten week old female C57Bl/6J or BALB/c/AnN mice were obtained from Jackson Laboratories (Bar Harbor, Me. or Sacramento, Calif.) or Taconic Laboratory (Oxnard, Calif.), respectively. Conventional animal chow and water were provided ad libitum. All protocols using animals have been approved by Merck & Co., Inc. and Merck Research Labs (MRL) Palo Alto Animal Use and Care Committee.

Before treatment, mice were weighed and tumors from individual mice were measured. To prevent bias, any outliers by weight or tumor volume were removed and the remaining mice randomized into various treatment groups with equivalent mean tumor size.

The test materials and isotype controls were obtained from MRL Palo Alto Protein Sciences department as frozen (−80° C.) stocks. The formulation buffers were specific for each antibody to stabilize proteins and prevent precipitation, the details of which are given below:

The formulations/diluents were obtained from MRL Palo Alto Protein Sciences department as stored at 4° C. The isotype control mIgG2a and anti-PD-1 formulation/diluent of 20 mM Na Acetate, 7% sucrose, pH5.5, mIgG1 formulation/diluent of 75 mM NaCl, 10 mM Phosphate, 3% sucrose, pH7.3, and the mDTA-1 (anti-mGITR) formulation/diluent of 20 mM NaAcetate, 7% sucrose, 0.02% Tween80 low peroxide, pH5.5 were for stabilizing the proteins and preventing from precipitation.

Example 3

Tumor Cell Line Preparation and Implant

MC38 or CT26 colon carcinoma cells were cultured in RPMI medium supplemented with 10% heat-inactivated fetal bovine serum. 1×1 MB49 bladder carcinoma cells were cultured in Dulbecco's Modified Eagle Medium (DMEM) supplemented with 10% fetal bovine serum and 1% Gluta-MAX™. $1\times10^6$ cells of MC38, $3\times10^5$ cells of CT26, or $0.5\times10^6$ cells of MB49 cells were injected SC in 100 µL volume of phosphate buffered saline in the left belly area or right flank of each mouse. Typically mice were first shaved with electronic clippers in the area that would be used for the implant.

Example 4

Tumor Measurements and Body Weights

Tumors were measured the day before the first dose and twice a week thereafter. Tumor length and width were measured using electronic calipers and tumor volume determined using the formula Volume $(mm^3)=0.5\times Length\times Width$ where length is the longer dimension.

Mice were weighed periodically to monitor general health but also to estimate actual mg/kg dose delivery per mouse where needed.

Example 5

Dosing Solution Preparation, Administration, and Analyses

Frozen stocks were thawed and transferred to wet ice. To avoid repeated freeze thaw, each vial of stock was thawed once and aliquots made in volumes sufficient for one time use. Polypropylene, low adhesion tubes were used for this purpose. The aliquots were snap frozen in dry ice and stored at 80° C. Before each dosing, one aliquot was thawed and diluted to nominal concentration in the appropriate diluent and dosed immediately. Aliquots of dosing solutions were snap frozen in dry ice and stored at −80° C. until analyses. Dosing solutions were assessed using the Meso Scale Discovery (MSD®, Rockville, Md.) platform which is based on multi-array technology; a combination of electrochemiluminescence detection and patterned arrays.

Dosing with the test materials started once the MC38 and CT26 tumors reached an average size of approximately 300 mm³ and 220 mm³, respectively, typically around two weeks post implant. Dosing with the test materials started once the MB49 tumors reached an average size of approximately 105 mm³, one week post implant. Variations in dosing frequency (ranging from a single dose to up to 6 weekly doses) at a dosing concentration of 5 mg/kg were tested, the details of which are given in below.

Example 6

Murinization of DTA-1 Antibody

Rat anti-mouse DTA-1 GITR antibody (S. Sakaguchi, Kyoto University, Kyoto, Japan), was murinized as follows. The sequence of rat antibody DTA-1 was determined for the variable heavy (VH) and variable light (VL) domains. The rat DTA-1 VH sequence was compared to mouse VH germline sequences from the Immunogenetics IMGT Database (Lefranc, M.-P. et al. (1999) *Nuc. Acids Res.* 27:209-212). DTA-1 VH sequence was aligned with the mouse VH germline sequences and scored similarly to a previous humanization system (see, e.g. WO 2005/047326). The rat DTA-1 VH was most similar to mouse germlines IGVH5-4, IGVH5-6 and IGVH5-9. CDR residues were transferred from rat DTA-1 VH to mouse germline IGVH5-4; two IGVH5-4 framework residues were altered to those fitting IGVH5-6 and mouse J-region IGHJ-4 (IMGT) was used to connect to mouse IgG1 and mouse IgG2a Fc regions.

The rat DTA-1 VL (lambda) sequence was aligned with mouse VL (lambda) sequence from GenBank: AAH02129.1. CDR residues were transferred from rat DTA-1 VL (lambda) to the mouse AAH02129 framework sequence. Seven framework residues on murinized DTA1 were altered based on computer graphic models of the rat and murinized VL domains. The murinized DTA-1 VL (lambda) domain was fused to mouse constant light domain.

For all three constructs (one VH and two VL (lambda)), codon-optimized genes were synthesized and inserted into expression vectors. Antibodies were expressed by transient expression in HEK293 cells and purified using protein-A chromatography.

Example 7

Anti-GITR/Anti-PD-1 Treatment Results

Advanced MC38 tumor-bearing C57BL/6J mice were treated with a single or two weekly injections of murinized anti-mGITR (Merck Research Labs, Palo Alto, Calif.) subcutaneously (SC), and murinized anti-mPD-1 (Merck Research Labs, Palo Alto, Calif.) intraperitoneally (IP), dosed at 5 mg/kg each. Treatment was started once the tumor sizes reached 240-360 mm³. Tumors were measured twice weekly. Complete regression (CR) of tumors served as a read-out for anti-tumor efficacy. Combination dosing led to robust, synergistic efficacy, with 100% CR after two weekly combination doses. Limiting the regimen to one dose of each antibody (Ab.) reduced CR to 70%, similar to that achieved with combination of anti-mGITR followed by four weekly administrations of anti-mPD-1 beginning one week later. A two week interval between anti-mGITR and anti-mPD-1 administration was not as effective. Only 20-30% CR was seen with monotherapy of up to six weekly treatments with anti-mGITR or 2-4 weekly treatments of anti-mPD-1 Ab (See FIGS. 1A-1K).

Advanced MC38 tumor-bearing C57BL/6J mice were treated with anti-mGITR (SC) and anti-mPD-1 (IP) dosed at 5 mg/kg each. Treatment was started once the tumor size reached 200-350 mm³. Tumors were measured twice weekly. Complete regression (CR) of tumors served as a read-out for anti-tumor efficacy. Combination dosing led to robust, synergistic efficacy, with 100% CR after two weekly combination doses. This is comparable to the results detailed above. However, a reduced CR of 60% was observed when the antibodies were delivered separately with a one week interval. Two weekly monotherapy doses of either anti-mGITR or anti-mPD-1 inhibited tumor growth but did not result in CRs (see FIGS. 2A-2F).

Advanced CT26 tumor-bearing BALB/cAnN mice were treated with anti-mGITR (SC) and anti-mPD-1 (IP) dosed at 5 mg/kg each. Treatment was started once the tumor size averaged 220 mm³ (180-260 mm³). Tumors were measured twice weekly. Complete regression (CR) of tumors served as a read-out for anti-tumor efficacy. A single combination dosing led to robust, synergistic efficacy, with 70% CR. The anti-tumor efficacy with either antibody delivered as monotherapy was 0-10% CR (see FIGS. 3A-3D).

MB49 tumor-bearing C57BL/6J mice were treated with a single dose of anti-GITR (SC) and anti-PD-1 (IP) at 5 mg/kg and 10 mg/kg respectively. Treatment was started once the tumor size averaged 105 mm³ (85-122 mm³). Tumors were measured twice weekly. Complete regression (CR) of tumors served as a read-out for anti-tumor efficacy. Anti-GITR and anti-PD-1 combination treatment led to enhanced efficacy with 40% CR. No CRs were observed in the single agent treatment groups (see FIGS. 4A-4D).

Example 8

Effect of Anti-PD-1 and Anti-GITR Combination on Regulatory T Cell and CD8 Cell Ratios A. Methods 1. Mixed Lymphocyte Reaction Cultures Peripheral blood mononuclear cells (PBMC) were isolated from buffy coats using Ficoll-Paque Plus density gradient centrifugation at 1200×g for 20 minutes. Peripheral blood mononuclear cells were collected from the medium: plasma interface and washed 2 times with Dulbecco's phosphate-buffered saline (DPBS). The residual red blood cells (RBCs) were lysed using Ammonium-chloride-potassium RBC lysing solution (RBC lysing solution).

Dendritic cells (DC) were generated from CD14+ monocytes using the following procedure. Monocytes were first isolated from buffy coats using RosetteSep human monocyte enrichment cocktail and Ficoll-Paque Plus density gradient centrifugation at 1200×g for 20 minutes. Monocytes were removed from the medium:plasma interface and washed 2 times with DPBS. The residual RBCs were lysed using RBC lysing solution. The enriched monocytes were cultured in Dulbecco's Modified Eagle Medium supplemented with 10% fetal bovine serum (FBS), 1,000 U/mL granulocyte-macrophage colony-stimulating factor (GM-CSF), and 400 U/mL interleukin (IL)-4 at a cell density of 2×10⁶/mL. At Day 6, 0.5 µg/mL lipopolysaccharide was added to the culture; the cells were then cultured for 2 more days.

Mixed lymphocyte reaction cultures were set up in 24-well plates. Peripheral blood mononuclear cells (2×10⁶/mL) were cultured with γ-irradiated (30 Gy) allogeneic DC (0.2×10⁶/mL) in the presence of 100 U/mL IL-2; 5 ng/mL IL-15; anti-hGITR antibody (MK-4166), anti-hPD-1 antibody (MK-3475), combination of MK-3475 and MK-4166 or isotype control mAb (anti-RSV). The number of regulatory T cells (Tregs) in MLR cultures was evaluated at Day 7 using flow cytometry.

2. Flow Cytometric Detection of T Regs in Mixed Lymphocyte Reaction Cultures

For the detection of Tregs (CD3+ CD4+ CD25+ FoxP3+) and CD8+ T cells, 1 to 2×10⁶ cells from MLR cultures were incubated with anti-CD3, anti-CD4, anti-CD25, and anti-CD8 in 50 µL of BD Pharmingen staining buffer. Dead cells were excluded using the Fixable Viability Dye eFluor 506. After surface staining with anti-CD3, anti-CD4, anti-CD8 and anti-CD25 mAbs, intracellular FoxP3 staining was performed using the FoxP3 Fixation/Permeabilization kit according to the manufacturer's instructions (eBioscience). Sample acquisition was performed on an LSR II flow cytometer and the data were analyzed using FlowJo software version 10.0.6 (Tree Star, Inc.). Tregs were identified by gating on CD3+CD4+ cells followed by gating on CD25+ FoxP3+ cells.

3. Regulatory T-Cell Suppression Assay

CD4+ T cells were isolated from buffy coats using RosetteSep human CD4+ T cells enrichment kit and Ficoll-Paque Plus density gradient centrifugation at 1200×g for 20 minutes. CD4+ T cells were collected from the medium:plasma interface and washed 2 times with DPBS. The residual RBCs were lysed using RBC lysing solution. CD4+ CD25+ Tregs and CD4+ CD25− effector T cells (Teffs) were separated using human CD25-conjugated microbeads II kit according to the manufacturer's instructions (Miltenyi Biotec). The purity of CD4+ CD25+ CD127− Tregs was approximately 40% to 70%. Human DCs were generated as described above.

For the T-cell suppression assays, a total 1×10⁵ T cells (Tregs and Teffs) and 2×10⁴ γ-irradiated (30 Gy) DCs per well were cultured in 96-well round-bottom plates for 7 days in the presence of MK-4166, MK-3475, combination of MK-3475 and MK-4166 or isotype control mAb (anti-RSV). CD4+ CD25− Teffs and CD4+ CD25+ Tregs were mixed at 4:1 ratio. On Day 6, tritium-labeled thymidine was added to the cultures for 20 hours. Following incubation with tritium-labeled thymidine, the cells were harvested, lysed using water, and analyzed using a β counter (PerkinElmer, 2450 microplate counter). The level of T-cell proliferation was reflected by the levels of incorporated tritium-labeled thymidine. All assays were conducted in triplicates.

B. Results

The ability of the anti-mouse GITR agonistic mAb DTA-1 to alter the stability and intratumoral accumulation of Tregs is essential for the mechanism of action of DTA-1 (see, e.g., Cohen et al (2010) *PLoS One* 5(e10436): 1-12; and Schaer et al. (2013) *Cancer Immunol. Res.* 1:320-331). The ability of MK-4166 alone or in combination with MK-3475 to impact the induction of human Tregs and their suppressive activity was investigated using human in vitro assay.

Figure 5A:
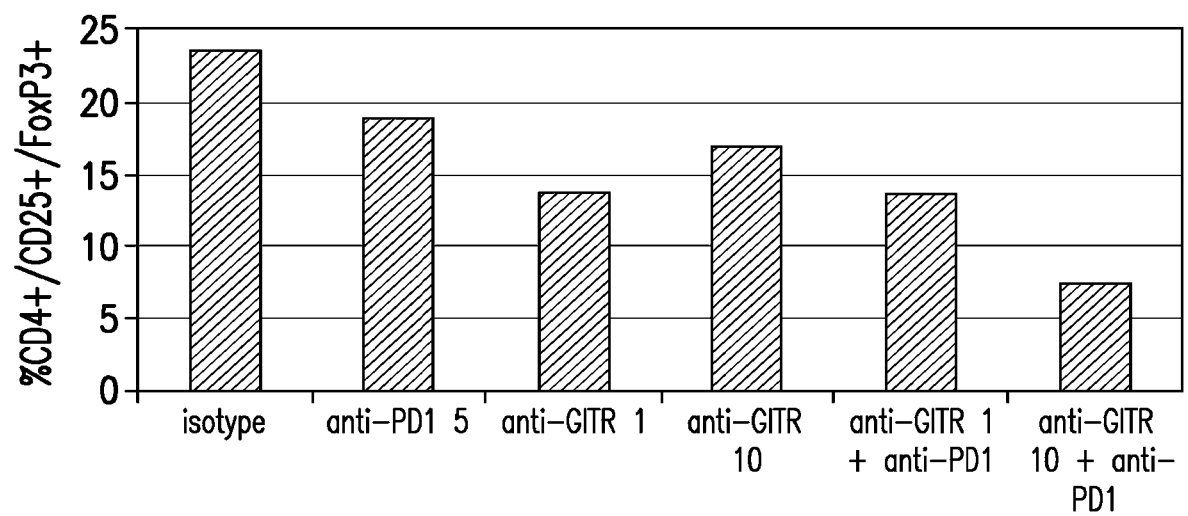
FIGS. 5A-5B show the dose dependent effect of the combination of anti-GITR (MK-4166) and anti-PD-1 (MK-3475) on Tregs (FIG. 5A) and Treg:CD8 cell ratio (FIG. 5B) in a mixed lymphocyte reaction (MLR).
Figure 5B:
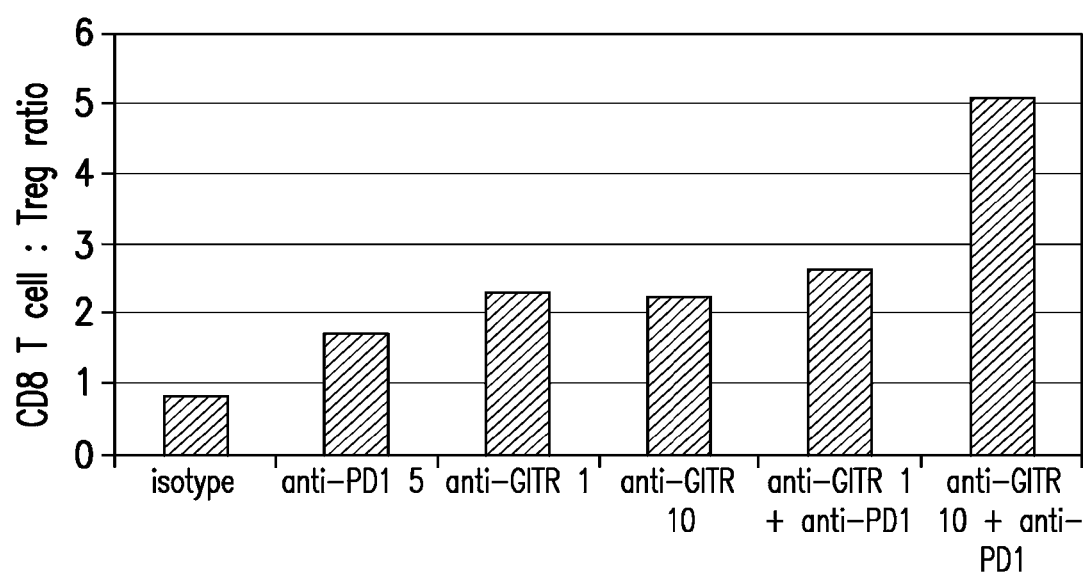

Induction of Tregs in MLR is well documented (see, e.g. Levitsky et al (2013) *Transplantation* 96:689-696). Thus, MLR was utilized to increase the number of human Tregs naturally occurring in blood and to assess the effect of MK-4166 alone or in combination with MK-3475 on human Tregs and CD8:Treg ratio. Addition of 10 µg/mL MK-4166 to MLR cultures resulted in decreased numbers of CD4+ CD25+ FoxP3+ Tregs after 7 days (FIG. 5A). MK-3475 alone did not have an effect on the number of Tregs. However combination of MK-3475 and MK-4166 had the most pronounced effect on the number of Tregs and CD8: Treg ratio (FIG. 5B).

Figure 6:
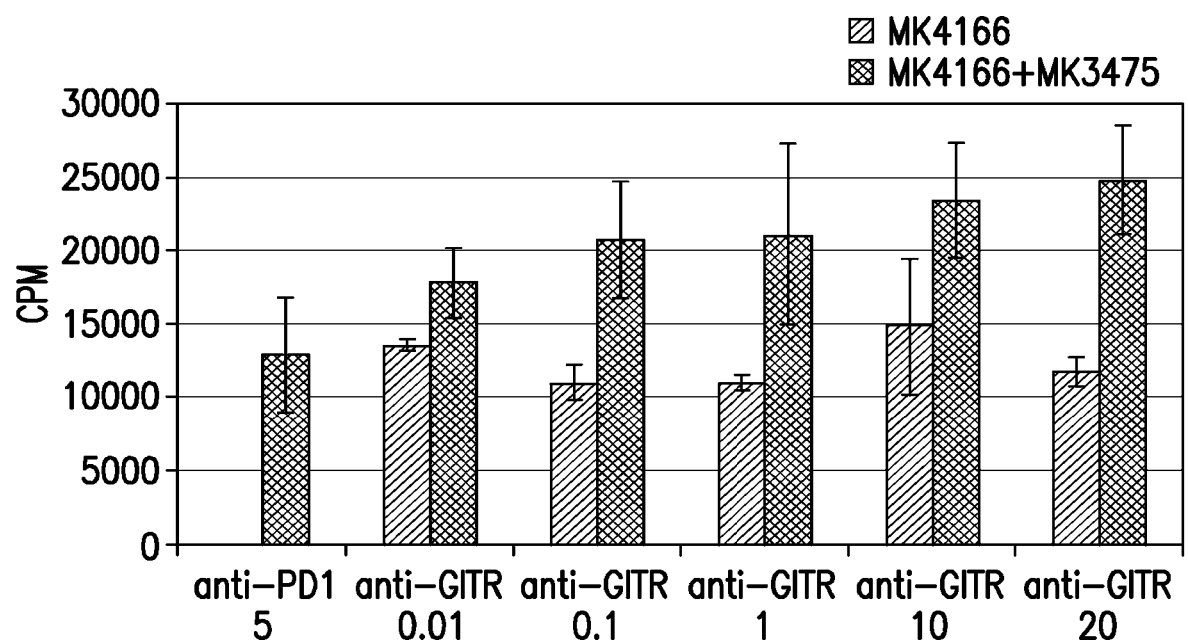
FIG. 6 shows that incubation with a combination of MK-4166 and MK-3475 results in reduced suppressive activity of Tregs in an MLR.

To evaluate the effect of MK-4166 on suppressive activity of human Tregs, the Treg suppression assay was established. In this assay, the level of T-cell proliferation is reflected by the levels of incorporated tritium-labeled thymidine. Dose-dependent increase in T cell proliferation was observed when MK-4166 was combined with MK-3475 (FIG. 6). These results provide evidence that incubation with MK-4166 and MK3475 decreases the number of MLR-induced Tregs, increases CD8:Treg ration and diminishes suppressive function of human Tregs in vitro.

Table 2 provides a brief description of the sequences in the sequence listing

| SEQ ID NO: | Description |
|---|---|
| 1 | 36E5 CDRH1 |
| 2 | 3D6 CDRH1 |
| 3 | 61G6 CDRH1 |
| 4 | 6H6 CDRH1 |
| 5 | 61F6 CDRH1 |
| 6 | 1D8 CDRH1 |
| 7 | 17F10 CDRH1 |
| 8 | 35D8 CDRH1 |
| 9 | 49A1 CDRH1 |
| 10 | 9E5 CDRH1 |
| 11 | 31H6 CDRH1 |
| 12 | 36E5 CDRH2 |
| 13 | 3D6 CDRH2 |
| 14 | 61G6 CDRH2 |
| 15 | 6H6 CDRH2 |
| 16 | 61F6 CDRH2 |
| 17 | 1D8 CDRH2 |
| 18 | 17F10 CDRH2 |
| 19 | 35D8 CDRH2 |
| 20 | 49A1 CDRH2 |
| 21 | 9E5 CDRH2 |
| 22 | 31H6 CDRH2 |
| 23 | 36E5 CDRH3 |
| 24 | 3D6 CDRH3 |
| 25 | 61G6 CDRH3 |
| 26 | 6H6 CDRH3 |
| 27 | 61F6 CDRH3 |
| 28 | 1D8 CDRH3 |
| 29 | 17F10 CDRH3 |
| 30 | 35D8 CDRH3 |
| 31 | 49A1 CDRH3 |
| 32 | 9E5 CDRH3 |
| 33 | 31H6 CDRH3 |
| 34 | 36E5 CDRL1 |
| 35 | 3D6 CDRL1 |
| 36 | 61G6 CDRL1 |
| 37 | 6H6 CDRL1 |
| 38 | 61F6 CDRL1 |
| 39 | 1D8 CDRL1 |
| 40 | 17F10 CDR L1 |
| 41 | 35D8 CDR L1 |
| 42 | 49A1 CDR L1 |
| 43 | 9E5 CDR L1 |
| 44 | 31H6 CDR L1 |
| 45 | 36E5 CDRL2 |
| 46 | 3D6 CDRL2 |
| 47 | 61G6 CDRL2 |
| 48 | 6H6 CDRL2 |
| 49 | 61F6 CDRL2 |
| 50 | 1D8 CDRL2 |
| 51 | 17F10 CDR L2 |
| 52 | 35D8 CDR L2 |
| 53 | 49A1 CDR L2 |
| 54 | 9E5 CDR L2 |
| 55 | 31H6 CDR L2 |
| 56 | 36E5 CDRL3 |
| 57 | 3D6 CDRL3 |
| 58 | 61G6 CDRL3 |
| 59 | 6H6 CDRL3 |
| 60 | 61F6 CDRL3 |
| 61 | 1D8 CDRL3 |
| 62 | 17F10 CDR L3 |
| 63 | 35D8 CDR L3 |

| SEQ ID NO: | Description |
|---|---|
| 64 | 49A1 CDR L3 |
| 65 | 9E5 CDR L3 |
| 66 | 31H6 CDR L3 |
| 67 | Humanized 1D8 VH |
| 68 | Humanized 1D8 VL |
| 69 | Humanized 3D6 VH |
| 70 | Humanized 3D6 VL |
| 71 | Humanized 6H6 VH |
| 72 | Humanized 6H6 VL |
| 73 | Humanized 9E5 VH |
| 74 | Humanized 9E5 VL |
| 75 | Humanized 31H6 VH |
| 76 | Humanized 31H6 VL |
| 77 | Humanized 17F10 VH |
| 78 | Humanized 17F10 VL |
| 79 | Humanized 35D8 VH |
| 80 | Humanized 35D8 VL |
| 81 | Humanized 36E5 VH |
| 82 | Humanized 36E5 VL |
| 83 | Humanized 49A1 VH |
| 84 | Humanized 49A1 VL |
| 85 | Humanized 61F6 VH |
| 86 | Humanized 61F6 VL |
| 87 | Humanized 61G6 VH |
| 88 | Humanized 61G6 VL |

What is claimed is:

1. A method of treating a tumor in a patient comprising administering to the patient a PD-1 antagonist and a GITR agonist, wherein the PD-1 antagonist is MK-3475 or antigen binding fragment thereof; wherein the GITR agonist is an antibody or antigen binding fragment thereof that comprises a light chain variable region that comprises CDR-L1, CDR-L2 and CDR-L3 of a light chain variable region of SEQ ID NO: 82 and a heavy chain variable region that comprises CDR-H1, CDR-H2 and CDR-H3 of a heavy chain variable region of SEQ ID NO:81; wherein CDR-L1 comprises amino acids 24-38 of SEQ ID NO:82 and amino acid 31 is N or Q, CDR-L2 comprises amino acids 54-60 of SEQ ID NO:82 and amino acid 57 is N or Q, CDR-L3 comprises amino acids 93-101 of SEQ ID NO:82, CDR-H1 comprises amino acids 26-35 of SEQ ID NO:81, CDR-H2 comprises amino acids 50-65 of SEQ ID NO:81, and CDR-H3 comprises amino acids 98-107 of SEQ ID NO:81; and wherein the PD-1 antagonist and GITR agonist are administered simultaneously or sequentially.

2. The method of claim 1, wherein the PD-1 antagonist and GITR agonist are administered simultaneously at least one time.

3. The method of claim 1, wherein the PD-1 antagonist and GITR agonist are administered simultaneously at least 2 times.

4. The method of claim 1, wherein the tumor is an advanced stage tumor.

5. The method of claim 4, wherein the advanced stage tumor is selected from the group consisting of squamous cell cancer, small-cell lung cancer, non-small cell lung cancer, gastrointestinal cancer, pancreatic cancer, glioblastoma, glioma, cervical cancer, ovarian cancer, liver cancer such as hepatic carcinoma and hepatoma, bladder cancer, breast cancer, colon cancer, colorectal cancer, endometrial carcinoma, myeloma, multiple myeloma, salivary gland carcinoma, kidney cancer, renal cell carcinoma, Wilms' tumors, basal cell carcinoma, melanoma, prostate cancer, vulval cancer, thyroid cancer, testicular cancer, and esophageal cancer.

6. The method of claim 1, wherein the GITR agonist is an antibody having:
   a) a heavy chain variable region of SEQ ID NO: 81; and
   b) a light chain variable region of SEQ ID NO: 82, wherein amino acid 31 of SEQ ID NO: 82 is Q and amino acid 57 of SEQ ID NO: 82 is Q.

7. The method of claim 1, wherein the GITR agonist is an antibody or antigen binding fragment thereof that comprises a light chain variable region that comprises CDR-L1 of SEQ ID NO:34, CDR-L2 of SEQ ID NO:45, and CDR-L3 of SEQ ID NO:56; and a heavy chain variable region that comprises CDR-H1 of SEQ ID NO:1, CDR-H2 of SEQ ID NO:12, and CDR-H3 of SEQ ID NO:23.

* * * * *